United States Patent
Seguela et al.

(10) Patent No.: US 7,547,521 B2
(45) Date of Patent: Jun. 16, 2009

(54) HETEROMULTIMERIC ION CHANNEL RECEPTOR AND USES THEREOF

(75) Inventors: Philippe Seguela, Outremont (CA); Kazimierz Babinski, Dorval (CA)

(73) Assignee: McGill University, Montreal, Quebec ( * ) Notice: Subject to any disclaimer, the term of this patent is extended or adjusted under 35 U.S.C. 154(b) by 608 days.

(21) Appl. No.: 10/258,073

(22) PCT Filed: Apr. 20, 2001

(86) PCT No.: PCT/CA01/00561

§ 371 (c)(1), (2), (4) Date: Apr. 28, 2003

(87) PCT Pub. No.: WO01/81570

PCT Pub. Date: Nov. 1, 2001

(65) Prior Publication Data

US 2003/0219858 A1    Nov. 27, 2003

(30) Foreign Application Priority Data

Apr. 20, 2000    (CA) .................................. 2304494

(51) Int. Cl.
*C07K 14/705* (2006.01)
*G01N 33/53* (2006.01)

(52) U.S. Cl. ...................... 435/7.2; 530/350

(58) Field of Classification Search .............. None
See application file for complete search history.

(56) References Cited

OTHER PUBLICATIONS

Alexander et al., Proc. Natl. Acad. Sci. 89(3352-3356)1992.*
Guo-HH et al. PNAS 101(25)9205-9210, 2004.*
Bowie et al., 1990, Science 247:1306-1310.*
K. Babinski, et al., "Mamalian ASIC2a and ASIC3 Subunits Co-assemble into Heteromeric Proton-gated Channels Sensitive to Gd3+," J. Biol. Chem. 275(37):28519-28525, 2000.
N. Le Novere and J.-P. Changeux, "The Ligand Gated Ion Channel Database," Nucl. Acids Res. 27(1):340-344, 1999.
S. J. Perry, et al., "A Human Gene Encoding Morphine Modulating Peptides Related to NPFF and FMRFamide," FEBS Let. 409:426-430, 1997.
T. Volk, et al., "Hypertonicity Activates Nonselective Cation Channels in Mouse Cortical Collecting Duct Cells," Proc. Natl. Acad. Sci. USA 92:8478-8482, 1995.

* cited by examiner

*Primary Examiner*—Michael Pak
(74) *Attorney, Agent, or Firm*—Lahive & Cockfield, LLP; Giulio A. DeConti, Jr., Esq.; Cynthia L. Kanik

(57) ABSTRACT

The present invention describes a heteromultimeric proton-gated ion channel (herein called ASIC-2S.2) with distinctive properties. Compositions and methods are provided for producing and expressing functional ASIC-2S.2 channels, composed of ASIC2A and ASIC3 subunits. The invention also provides genetically engineered expression vectors comprising the nucleic acid sequences encoding both ASIC2A and ASIC3 and host cells coexpressing both ASIC2A and ASIC3 subunits. Also provided herein are genetically engineered nucleic acids encoding chimeric proton-gated ion channels comprised of at least two different subunits, as well as expression vectors and host cells comprising said engineered nucleic acids. The invention also provides for the use of ASIC-2S.2, as well as agonists, antagonists or antibodies specifically binding ASIC-2S.2, in the diagnosis, prevention and treatment of diseases associated with expression of ASIC-2S.2. Also are disclosed methods of influencing electrophysiological, pharmacological and/or functional properties of ASIC-2S.2 as well as methods for screening for substances having ion-channel modulating activity or substances capable of disrupting subunit association or interaction.

11 Claims, 17 Drawing Sheets

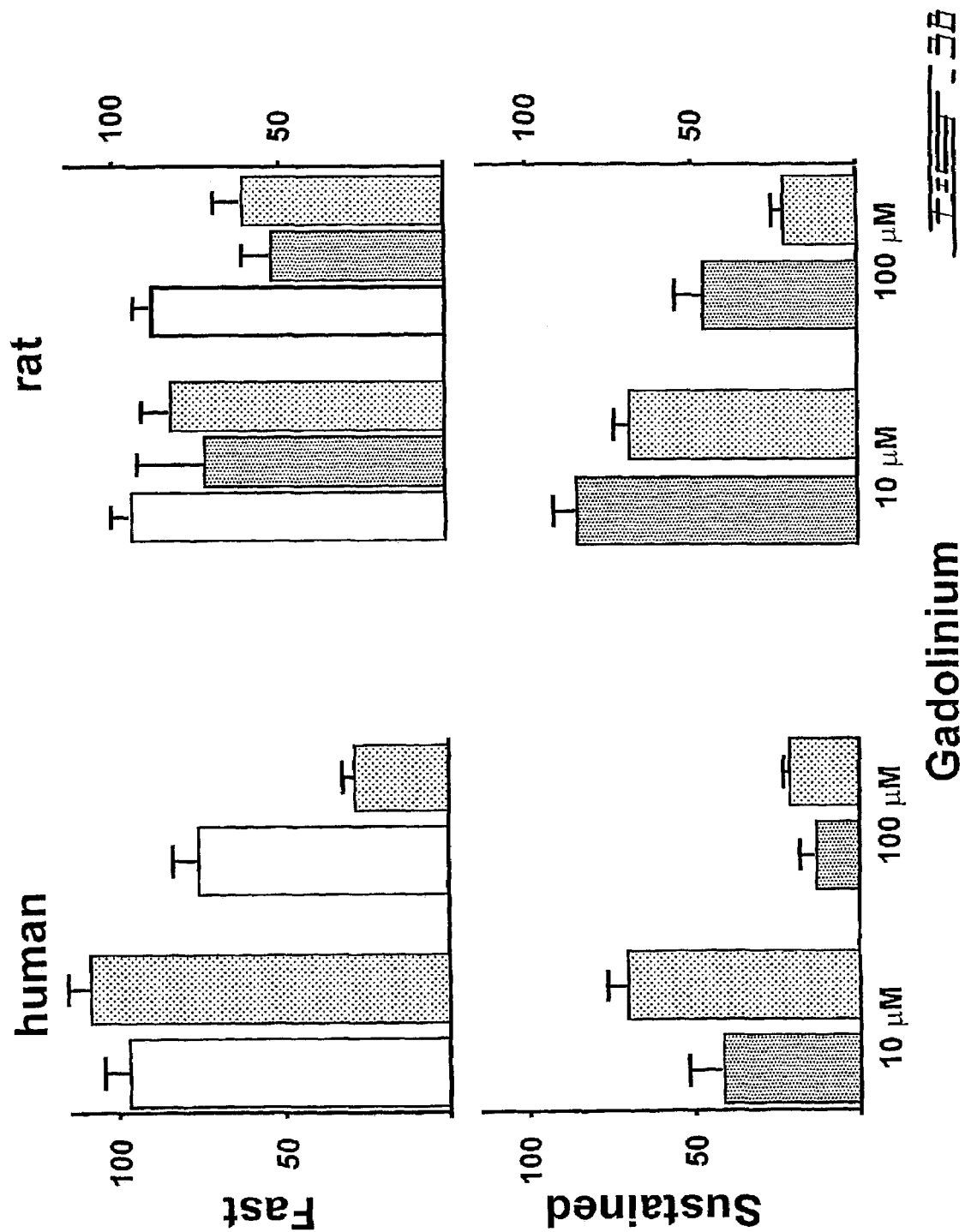

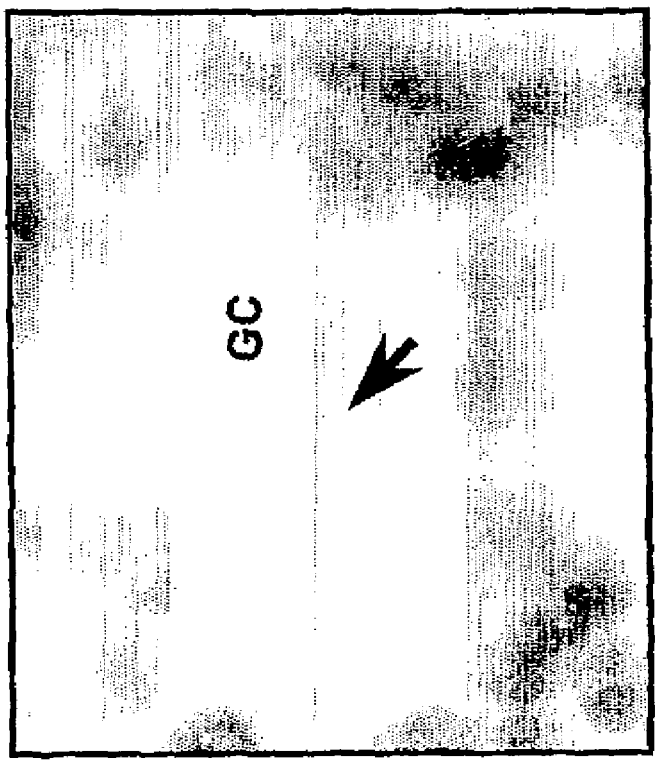
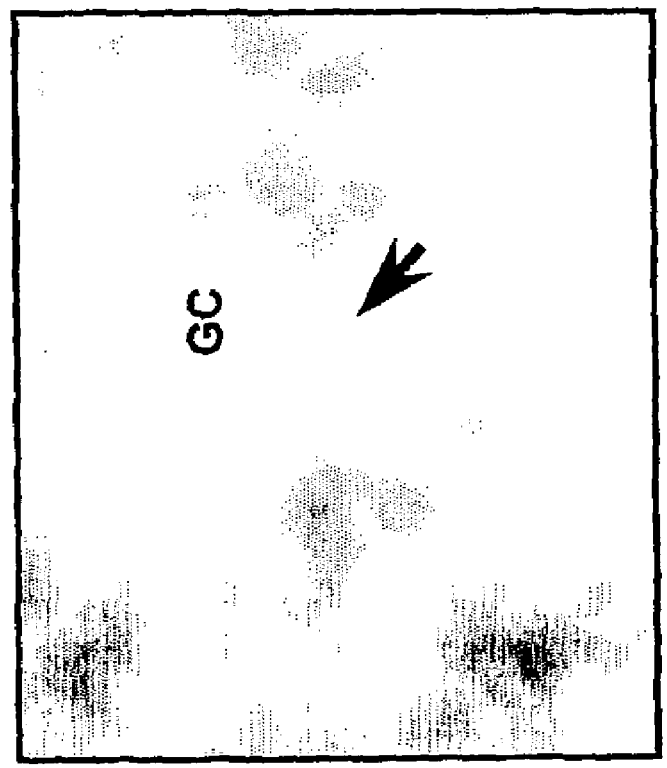
FIG. 5

|  | Wild Type | | N-Terminal Tag | | | C-Terminal Tag | | | |
|---|---|---|---|---|---|---|---|---|---|
|  | ASIC 2A-WT | ASIC 3-WT | GFP-ASIC 2A | His-ASIC 2A | His-ASIC 3 | ASIC 2A-Flag | ASIC 2A-His | ASIC 3-Flag | ASIC 3-His |
| Wild Type ASIC 2A-WT | 2A | 2A3 |  |  |  |  |  | 2A3 | 2A |
| Wild Type ASIC 3-WT |  | 3 | 2A3 |  |  |  | 3 |  |  |
| N-Terminal Tag GFP-ASIC 2A |  |  | 2A | 2A3 |  |  | 2A3 |  |  |
| N-Terminal Tag His-ASIC 2A |  |  |  | 2A |  |  |  |  |  |
| N-Terminal Tag His-ASIC 3 |  |  |  |  | 3 |  |  |  |  |
| C-terminal Tag ASIC 2A-Flag |  |  |  |  |  | ☒ |  |  |  |
| C-terminal Tag ASIC 2A-His |  |  |  |  |  | ☒ | ☒ |  |  |
| C-terminal Tag ASIC 3-Flag |  |  |  |  |  |  |  | 3 |  |
| C-terminal Tag ASIC 3-His |  |  |  |  |  |  |  |  | ☒ |

Homomultimeric channels tested
Heteromultimeric channels tested
Heteromultimeric channels not tested
☒ No current was recorded
2A ASIC2A-like inward current
3 ASIC3-like inward current
2A3 ASIC2A + ASIC3 heteromeric-like current
} Proton-activated

FIG. 6B

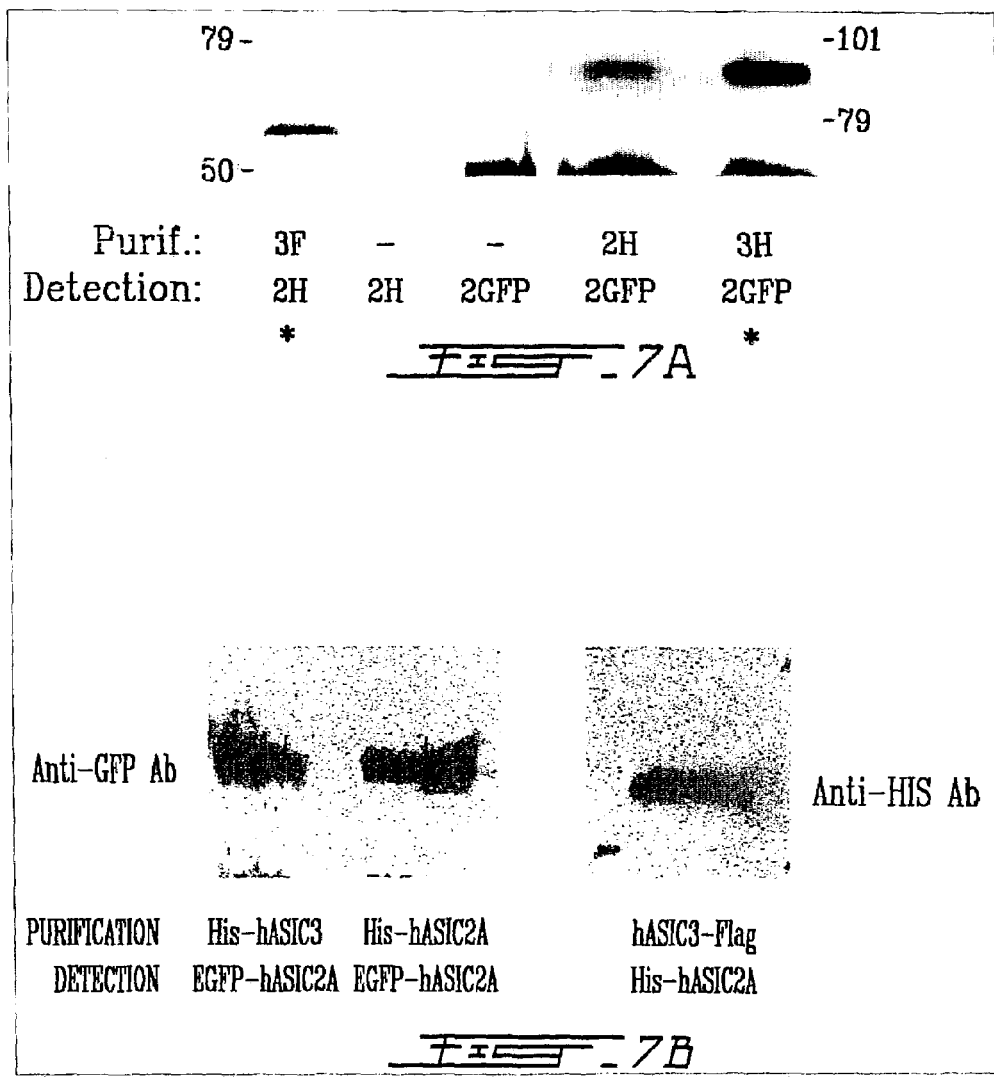

| Nomenclature in the present invention | Species | Synonym and/or equivalent | GenBank Accession Nos. | Reference | Applicable Patents |
|---|---|---|---|---|---|
| hASIC2A | human | BNC 1<br>BNaC1<br>MDEG | U50352<br>U57352<br>U53212 | JBC 1996; 271: 7879<br>PNAS 1997; 94: 1459<br>JBC 1996; 271: 10433 | US5892018 |
| hASIC3 | human | hASIC3<br>hASIC3<br>hTNaC1 | AF057711<br>AF095897<br>AB010575 | J Neurochem 1999; 72: 51<br>FEBS Lett 1998; 433: 257<br>BBRC 1998; 245: 589 | WO9921981 |
| rASIC2A | rat | MDEG<br>MDEG 1 | U53211<br>U53212 | JBC 1996; 271: 10433<br>JBC 1996; 271: 10433 | WO9835034<br>WO9835035 |
| rASIC3 | rat | DRASIC | AF013598 | JBC 1997; 272: 20975 | WO9835034 |
| ASIC2A | all | When used without species prefix, ASIC2A or ASIC3 encompass the orthologues /homologues of all species, including human and rat. | | | |
| ASIC3 | all | | | | |
| ASIC-2S.2 | all | Heteromultimeric ASIC receptor comprised of ASIC2A and ASIC3 subunits, as described above | | | |

Fig. 8

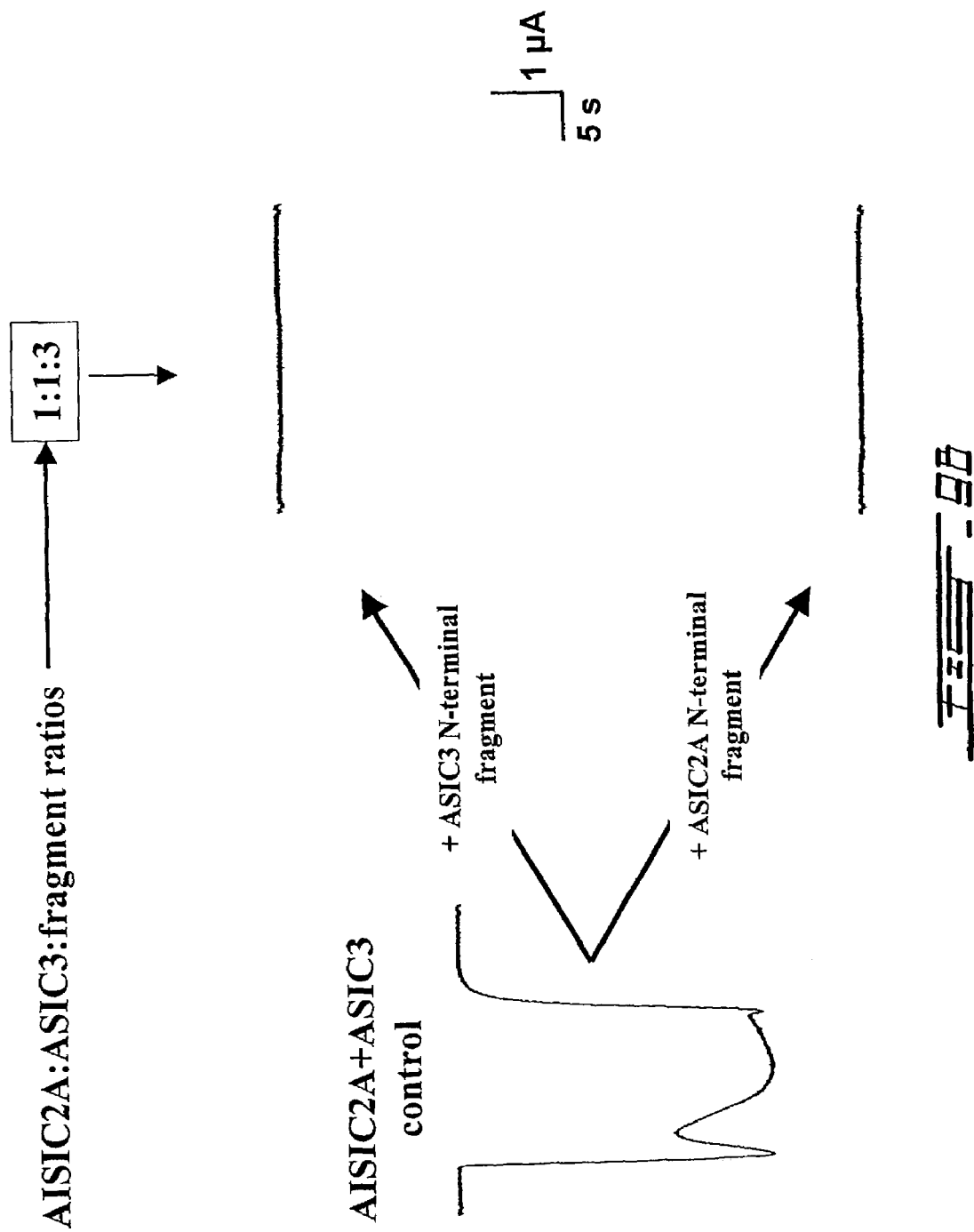

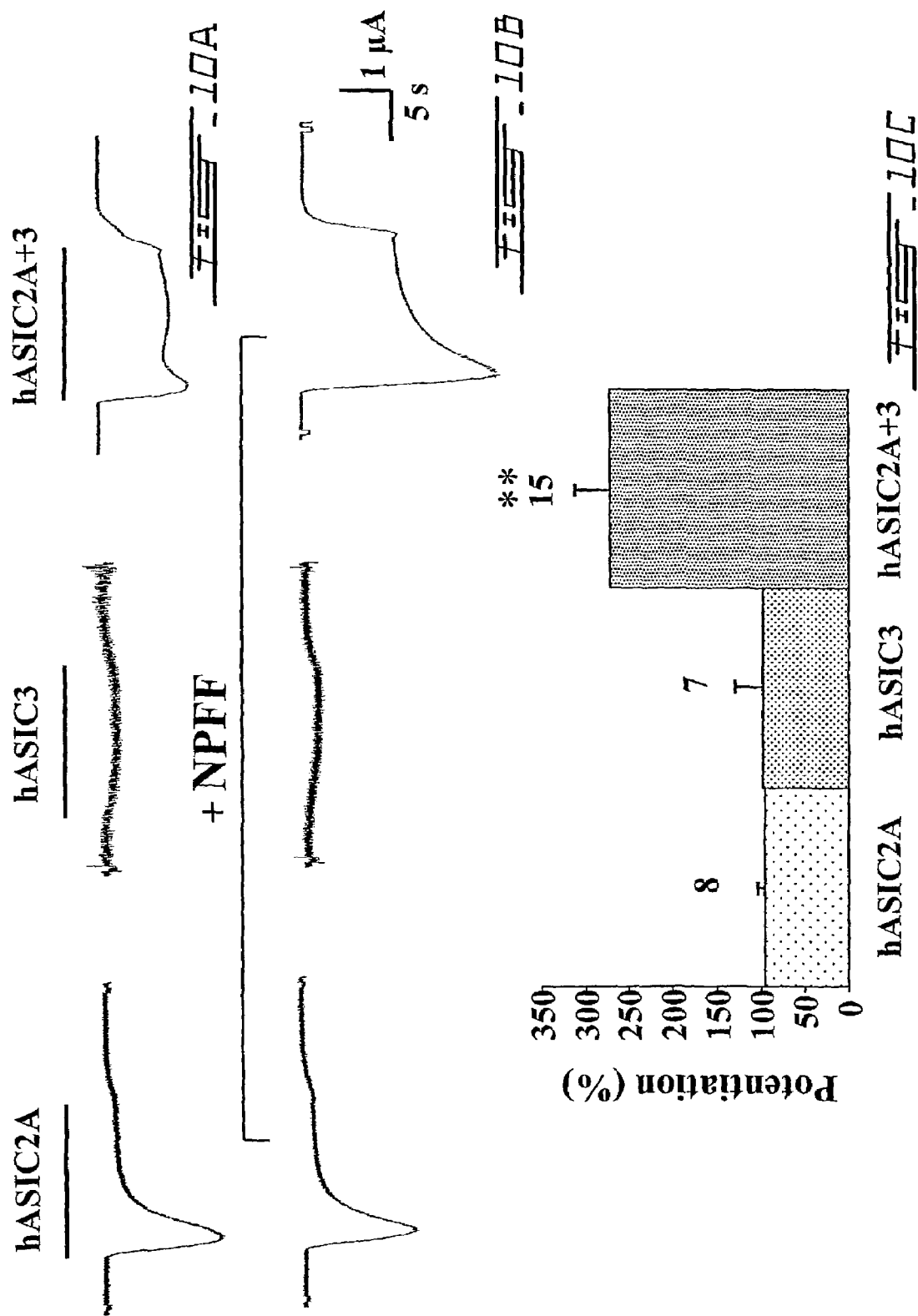

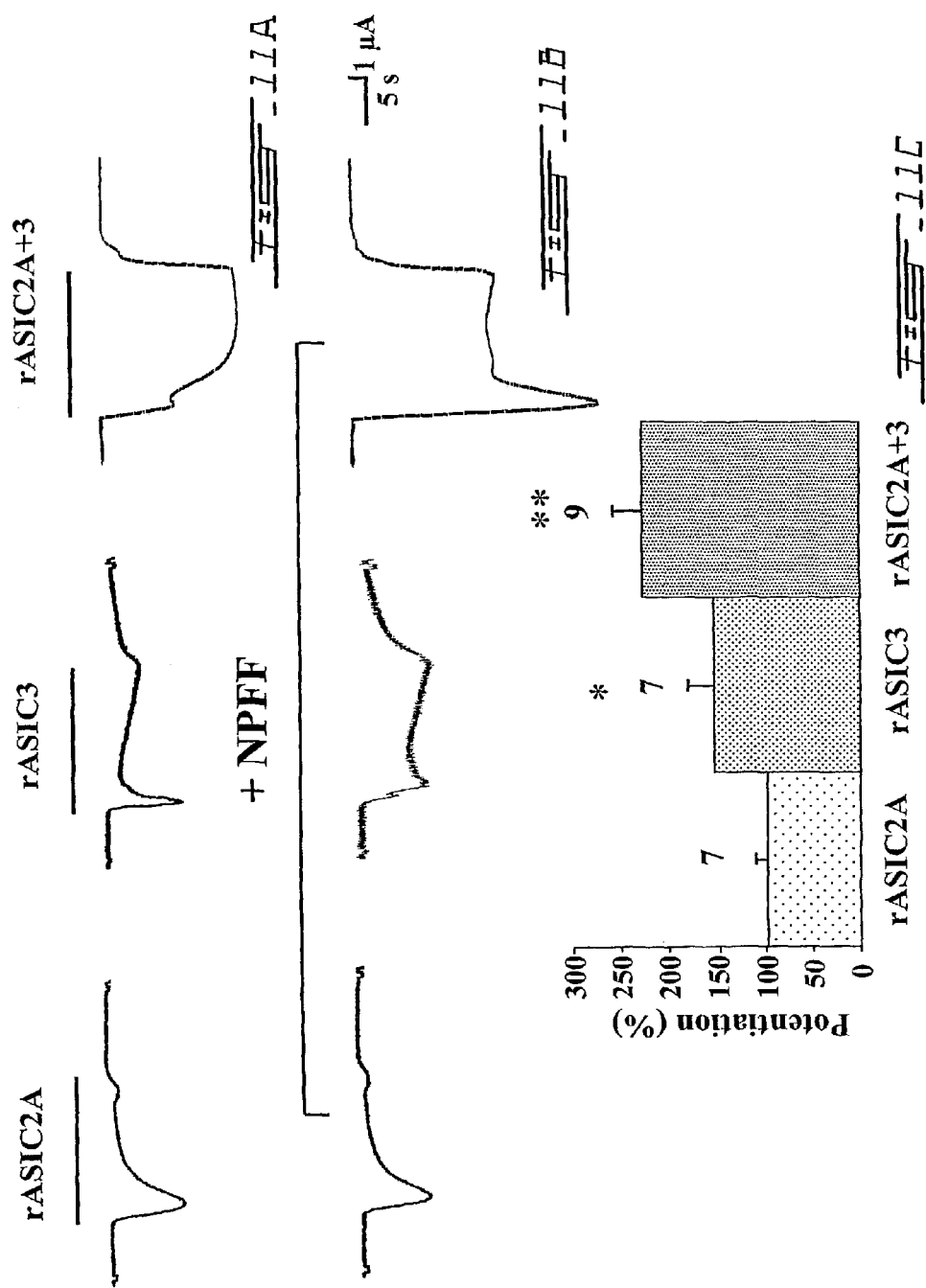

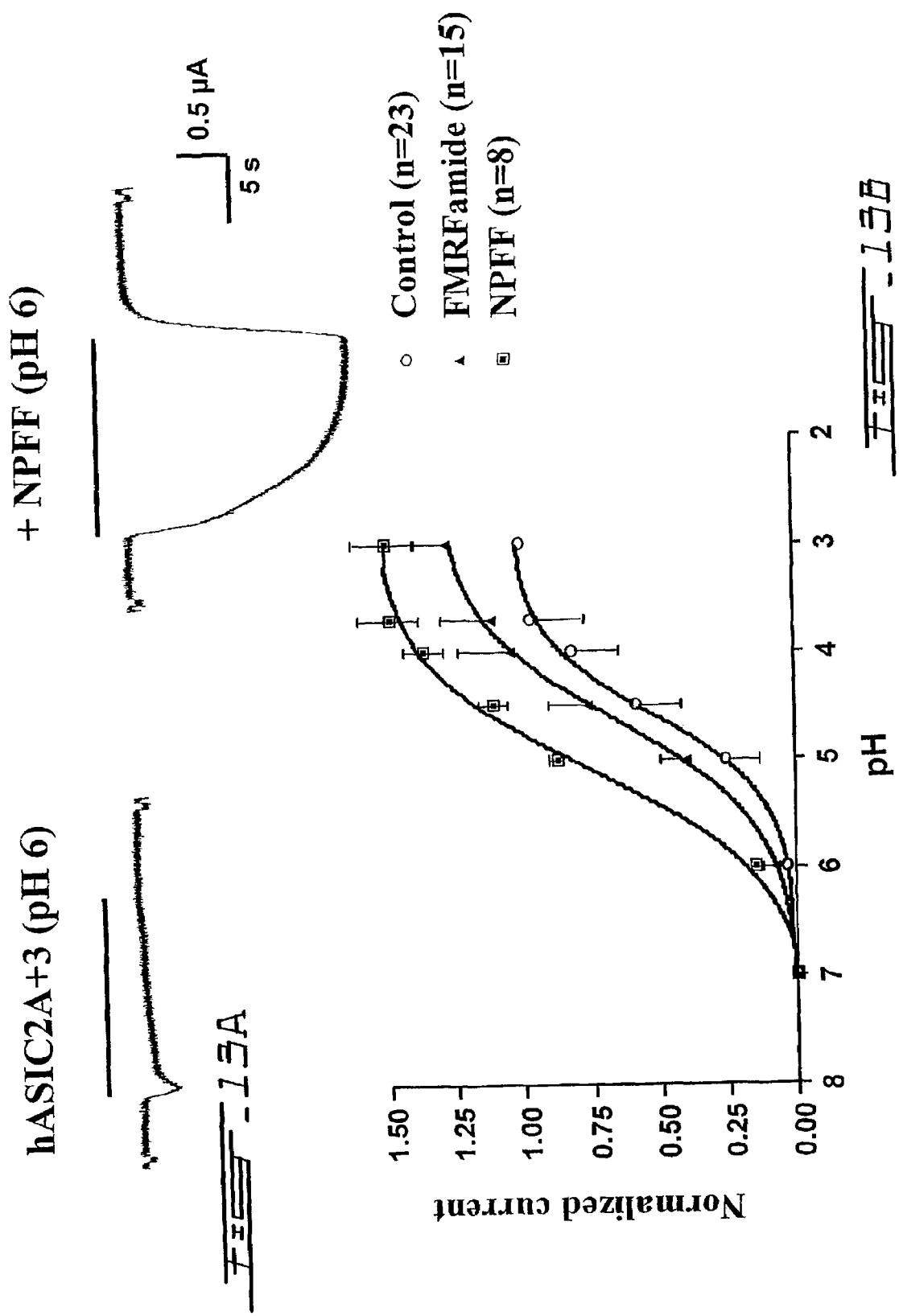

HETEROMULTIMERIC ION CHANNEL RECEPTOR AND USES THEREOF

FIELD OF THE INVENTION

The present invention is based on the discovery of a novel Acid Sensing Ion Channel (ASIC) with distinctive channel properties and biological activity. This novel channel, ASIC-2S.2 is a heteromultimeric complex comprised of two different types of ASIC subunits, namely ASIC2A and ASIC3. The present invention is also based on the discovery of a new use of polynucleotides encoding ASIC2A and ASIC3, said use being the inclusion of ASIC2A and ASIC3 in the assembly of a heteromultimeric ion channel. This invention further includes the use of the above compositions for diagnosis, prevention, or treatment of diseases related to the expression of the heteromultimeric ASIC channel disclosed herein.

The present invention demonstrates for the first time the direct biochemical interaction between two distinct ASIC subunits, namely ASIC2A and ASIC3, which produces a novel proton-gated ion channel with distinctive properties.

BACKGROUND OF INVENTION

In mammals, the pH of the extracellular compartment, including interstitial fluids and blood, is strictly regulated and maintained at a constant value of 7.4. Acid sensing is a specific kind of chemoreception that plays a critical role in the detection of nociceptive pH imbalances occurring, for example, in conditions of cramps, trauma, inflammation or hypoxia (Lindahl, Adv Neurol 1974; 4: 45)). In mammals, a population of small-diameter primary sensory neurons in the dorsal root ganglia and trigeminal ganglia (Bevan and Yeats, J Physiol (Lond) 1991; 433: 145) as well as central neurons (Varming, Neuropharmacol 1999; 38: 1875) express specialized pH-sensitive surface receptors activated by an increase of extracellular proton concentrations. Acid sensitivity of sensory as well as central neurons is mediated by a family of proton-gated cation channels structurally related to *C. elegans* degenerins (DEG) and mammalian epithelial sodium channels (ENaC). This invention relates to these Acid Sensing Ion Channels (ASIC) and specifically reports the discovery of novel class of receptors generated by the heteromultimeric assembly of two distinct ASIC subunits, namely ASIC2A (or BnaC1, or BNC1, or MDEG, or MDEG1) and ASIC3 (or hASIC3, or DRASIC) and uses thereof.

Tissue acidosis is associated with a number of painful, physiological (e.g. cramps) and pathological conditions (e.g. inflammation, intermittent claudication, myocardial infarction). Experimentally, similar painful events can be reproduced by infusing low pH solutions into skin or muscle. Furthermore, the prolonged intradermal infusion of low pH solutions can mimic the characteristic hyperalgesia of chronic pain. To further characterize the effects of protons and their relation to pain, low pH solutions were applied to patch-clamped central and peripheral sensory neurons. Inward currents were induced when pH was dropped to acidic values, providing evidence for the existence of proton-activated ion channels. Several types of native currents were observed in sensory neurons from rat and human trigeminal and dorsal root ganglia as well as central neurons: rapidly inactivating currents; non-inactivating currents; and biphasic currents displaying a rapidly inactivating current followed by non-inactivating sustained current. Other differences regarding ion selectivities were also reported. These results suggested the existence of a multigene family of proton-gated ion channels, implicated in neurotransmission and/or neuromodulation.

Cloned Proton-gated Ion Channels

The mammalian proton-gated cation channels have recently been cloned and named <<ASIC>> for Acid Sensing Ion Channels. Sequence analysis identifies them as members of the DEG/ENaC superfamily of ion channels. The putative membrane topology of ASIC receptors predicts two transmembrane spanning domains with both N- and C-termini in the intracellular compartment, as shown for the epithelial sodium channels. Four sub-classes of ASIC receptors have been identified:

1. ASIC1 ion channels display rapidly inactivating inward currents (Waldmann et al., Nature 1997; 386:173)
2. ASIC2 ion channels display slowly inactivating inward currents (Brassilana et al., J Biol Chem 1997; 272: 28819).
3. ASIC3 ion channels display biphasic inward currents with an initial rapidly inactivating component, followed by a sustained non-inactivating current (Waldmann et al., J Biol Chem 1997; 272: 20975; Babinski et al., J Neurochem 1999; 72: 51)
4. ASIC4 ion channels displaying similar properties as those of ASIC3 (Wood et al., WO9963081)

Other recently discovered ion channel subunits, BLINaC and INaC, appear to belong to the ASIC family but are not activated by protons and have not yet been shown to interact with other ASIC subunits (Sakai et al., J Physiol 1999; 519: 323, Schaefer et al., FEBS Lett 2000; In Press).

Families of ASIC Receptors Created by Alternative Splicing of mRNAs

A common feature of these ion channels is the existence of alternative splice variants, which display important functional differences. Indeed, the replacement of the first 185 amino acids of ASIC1 (hereinafter named ASIC1A) by a distinct new sequence of 172 amino acids generates a new channel, ASIC1B, which has similar current kinetics as ASIC1A but needs lower pH values for activation ($pH_{50}$ of 6.2 and 4.5, respectively, for ASIC1A and ASIC1B). Also, it appears that ASIC1B is specifically expressed in rat dorsal root ganglia. A similar situation is also observed with rat ASIC2 (hereinafter named ASIC2A), where the replacement of the first 185 amino acids by a distinct new sequence of 236 amino acids generates another ASIC ion channel subunit, ASIC2B. When expressed alone as a homomultimer in mammalian cells or *Xenopus* oocytes, ASIC2B does not appear to be activated by low pH solutions. ASIC3, which has been identified in human, also appears to exist in various forms. Indeed, DRASIC is an ASIC3-like channel identified in rat, which displays 85% identity with the human ASIC3 sequence and has similar biphasic current kinetics. However, important differences regarding tissue distribution, ion selectivities and $pH_{50}$ suggest that DRASIC might not be the human orthologue of ASIC3 but rather a different subtype. Furthermore, the existence of two 3' splice variants of human ASIC3 (ASIC3B and 3C, sequences submitted to GenBank) have been reported but differences in function have yet to be documented. Alternative splicing, therefore, appears like an important mechanism for increasing the diversity of ASIC receptors, which most probably assume critical roles in the nervous system, such as neurotransmission, nociception or mechanosensation (see below).

Families of ASIC Receptors Created by Heteromultemeric Associations

In general, functional ion channels are complex structures comprised of several individual components, referred) to as subunits. The number of subunits depends on the type of ion channel and subunits can either be all identical (homomultimeric channels) or include a combination of several different subtypes (heteromultimeric channels). For example, Epithelial sodium Channels (ENaC), which belong to the same gene family as ASIC receptors, are comprised of at least three different subunits, namely αEnaC, βEnaC and γEnaC (Canessa et al., Nature 1994; 367: 463). Although cloned ASIC receptors have mostly been characterized in vitro in their homomultimeric form, the analogy with EnaCs raises the possibilty that ASIC subunits might also associate in various combinations to generate novel channels with distinctive properties. Indeed, heteromultimeric ASIC channels might account for some of the native proton-gated currents still not explained by any of the homomultimeric ASICs cloned to date. Examples of such native currents are the sustained non-desensitizing currents seen at pH 6 (Bevan and Yeats, J Physiol 1991; 433: 145). Furthermore, the discovery of the proton-insensitive ASIC2B (or MDEG2) suggests that it may function as an accessory subunit. Indeed, the first evidence for heteromultimeric ASIC receptors came from coexpression studies featuring rat ASIC2B either with ASIC2A or with ASIC3. Channels created by ASIC2A and ASIC2B appear to be slightly more sensitive to pH, while inward currents carried by ASIC2B+ASIC3 channels are apparently less sodium selective than the homomultimeric ASIC3 currents (Lingueglia et al., J Biol Chem 1997: 272: 29778). However, no biochemical evidence of interaction has been reported to date for any ASIC subunits. Furthermore, other coexpression experiments with different subunits suggest that not all subunit combinations yield novel functional channels. Thus, the composition and functional characteristics of heteromultimeric ASIC channels are therefore unpredictable.

SUMMARY OF THE INVENTION

It is the purpose of the present invention to disclose and describe a novel heteromultimeric ASIC channel, herein called ASIC-2S.2, and uses thereof.

The present invention reports the discovery of a novel heteromultimeric ASIC receptor (hereinafter called ASIC-2S.2). Also contemplated within the scope of this invention is the potential involvement of this new receptor in neurotransmission and/or nociception and/or mechanosensation and/or any other neurological and/or metabolic processes in normal and/or pathophysiological conditions. This invention seeks also to cover any uses of this new ion channel as a therapeutic target, including but not limited to drug screening technologies (i.e. screening for channel antagonists, agonists, modulators and/or subunit association blockers), diagnostic marker, or gene therapies. Also within the scope of the present invention is the heteropolymerization of the ASIC-2S.2 channel with one or more additional subunits of the ASIC family from any species, including but not limited to ASIC1, ASIC1A, BNaC2, ASIC1B, ASIC2B, MDEG2, ASIC4, SPA-SIC or any variants thereof, as well as heteropolymerization of ASIC-2S.2 with any other members of the Degenerin and EnaC family from any species.

An object of this invention is therefore to provide the composition of the novel ASIC-2S.2 receptor and methods of producing and expressing functional ASIC-2S.2 ion channels.

Another object of the present invention is to provide methods for engineering nucleic acids specifically designed to encode a chimeric ASIC receptor comprised of a single polypeptide, where two or more ASIC subunits are covalently linked together, and expressed in tandem as a single amino acid sequence.

Also included within the scope of this invention are methods designed for screening and identifying substances, whether chemically synthetised or isolated from natural sources, which have ion channel modulating activity. Typically this includes but is not limited to competitive and non-competitive agonists and partial agonists as well as competitive and non-competitive antagonists and partial antagonists, as well any substance capable of directly or indirectly disrupting, inhibiting or preventing the complete or partial association of ASIC subunits, as disclosed hereinafter, into functional, partially functional, or non-functional channels.

The invention additionally features the specific use of nucleic acids encoding the ASIC subunits comprising the ASIC-2S.2 heteromultimeric channel, namely ASIC2A (BNaC1, MDEG1) and ASIC3 (or DRASIC), as well as polypeptides, oligonucleotides, peptide nucleic acids (PNA), fragments, portions, antisense molecules, or any derivatives thereof, where specific use includes disruption, inhibition or prevention of ASIC subunit association or assembly into the ASIC-2S.2 heteromultimeric channels of the present invention. Also within the scope of this invention are expression vectors and host cells comprising nucleic acids that simultaneously encode and/or express ASIC2A and ASIC3 subunits together. The present invention also features pharmaceutical compositions comprising substantially purified ASIC-2S.2 as well as antibodies which bind specifically to the ASIC subunits of the ASIC-2S.2 channel complex and whose specific binding causes the disruption, inhibition or prevention of ASIC subunit association or assembly into the ASIC-2S.2 heteromultimeric channels of the present invention

DESCRIPTION OF THE FIGURES

The following drawings, figures and tables are illustrative of the embodiments of the invention and are not meant to limit the scope of the invention as encompassed by the claims.

FIG. 1 illustrates the pH-activated inward currents recorded in voltage clamped *Xenopus* oocytes expressing ASIC2A and ASIC3, either alone or in combination. The functional interaction is clearly visible when comparing currents between mono-injected and co-injected oocytes.

FIG. 5 reveals In situ hybridization in rat cerebellum with MDEG1- and DRASIC-specific probes showing the co-expression of both subunits in the same cell type.

FIG. 6 illustrates the effects of N- or C-terminal tagging of ASIC2A and/or ASIC3 subunits on proton-activated inward currents recorded using voltage clamped Xenopus oocytes expressing either the homomultimeric or heteromultimeric ASIC channels.

FIG. 7 is a Western blot of N-terminally tagged hASIC2A and hASIC3 subunits coexpressed in Xenopus oocytes (A) or HEK293 cells (B), showing that both subunits are co-immunoprecipitated or co-purified, providing evidence in favour of a direct biochemical interaction between subunits.

FIG. 8 is a Table listing all the synonyms of ASIC2A and ASIC3 used in various publications, databases, patent applications and patents.

FIG. 9 shows the inhibitory effects of C-terminal and N-terminal fragments of ASIC2A or ASIC3 on the current mediated by ASIC2S.2 heteromoeric channel. Any given vectors carrying the fragments was co-injected with the ASIC2A and ASIC3 subunits and tested at two different ratios of fragment versus ASIC2A and ASIC3 subunit. FIG. 9B shows the effects of the N-terminal fragments of ASIC3 (upper traces) and ASIC2A (lower traces).

FIG. 10 reveals the selective modulatory effect of 10 µM NPFF on the proton-gated cationic currents evoked by human heteromeric ASIC receptors expressed in Xenopus oocytes . A. Human homomeric ASIC2A, ASIC3 and heteromeric ASIC2S.2 (ASIC2A+3) response to pH 4 application (bar). B. Same as in A but in the presence of NPFF. Note the change in desensitization kinetics in presence of the peptide and the potentiation of the current mediated by heteromeric ASIC2S.2. C. Quantitative effects of NPFF on peak currents evoked by acidic pH for the three subtypes of human ASICs. Values expressed as % of control are mean±SEM FIG. 11 shows the modulatory effect of 10 µM NPFF on the proton-gated cationic currents evoked by rat homomeric ASIC3 and heteromeric ASIC2S.2 (ASIC2A+3) receptors expressed in Xenopus oocytes . A. rat homomeric ASIC2A, ASIC3 and heteromeric ASIC2S.2 response to pH 4 application (bar). B. Same as in A but in the presence of NPFF. Note the more pronounced potentiation of the current mediated by heteromeric ASIC2S.2 than by homomeric ASIC3. C. Histograms illustrating the effects of NPFF on peak currents evoked by acidic pH for the three subtypes of rat ASICs. Values expressed as % of control are mean±SEM.

FIG. 13A. NPFF potentiated the response of human ASIC2S.2 (ASIC2A+3) receptors to pH 6 stimulation. B. pH dose-response curves of human heteromeric ASIC2S.2 (ASIC2A+3) receptors in the presence or absence of neuropeptides. Sensitivity and maximal response to acidification increased in presence of 100 µM FMRFamide and the effects were even greater in the presence of 10 µM NPFF. Reference value for current normalization corresponded to maximal control currents induced at pH 3. Values are expressed as mean±SEM.

DETAILED DESCRIPTION OF THE INVENTION

Preambule

Figure 1A:
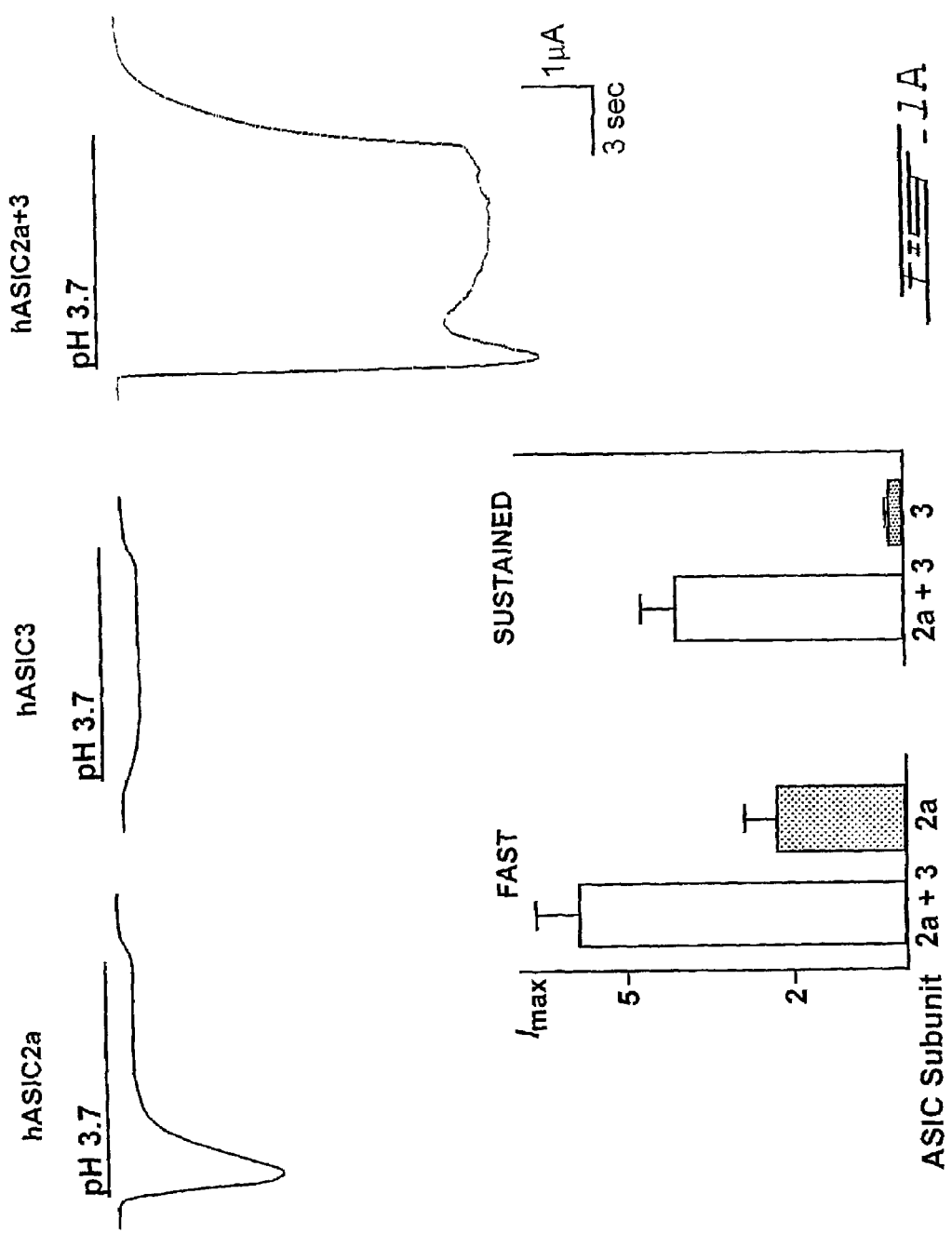
FIG. 1A: Human subunits, BNaC1 and hASIC3.
Figure 1B:
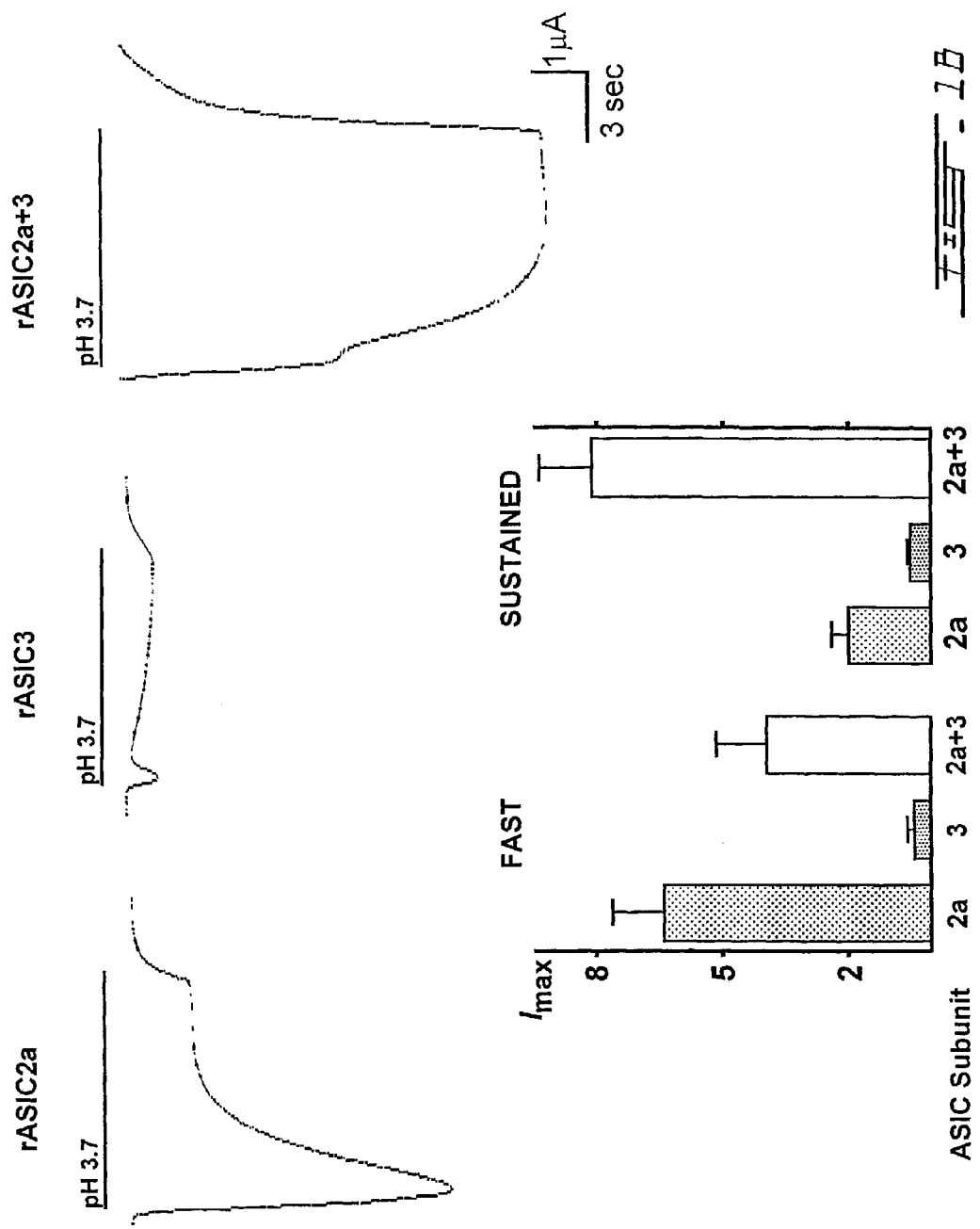
FIG. 1B: Rat subunits, MDEG1 and DRASIC.

It is understood that the present invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells; reference to "the antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

Definitions

For the sake of clarity, FIG. 8 summarises the nomenclature of the ASIC subunits encompassed by the present invention and will be applied to identify without ambiguity the ASIC subunits herein referred to. Unless specified otherwise, reference to an ASIC subunit is not intended to be limited to a particular species but includes the orthologues or homologues of any species.

"Polynucleotide" and "nucleic acids" as used herein refers to single- or double-stranded molecules which may be "deoxyribonucleic acid" (DNA), comprised of the nucleotide bases A, T, C and G, or "ribonucleic acid" (RNA), comprised of bases A, U (substitutes for T), C and G. Polynucleotides may represent a coding strand or its complement, the sense or anti-sense strands. Polynucleotides may be identical in sequence to the sequence which is naturally occurring or may include alternative codons which encode the same amino acid as that which is found in the naturally occurring sequence (Lewin: "Genes V", Chapter 7; Oxford University Press, 1994). Furthermore, polynucleotides may include codons which represent conservative substitutions of amino acids. The term "polynucleotide" will also include all possible alternate forms of DNA or RNA, such as genomic DNA (both introns and exons), complementary DNA (cDNA), cRNA, messenger RNA (mRNA), and DNA or RNA prepared by partial or total chemical synthesis from nucleotide bases, including modified bases, such as tritylated bases and unusual bases such as inosine. Polynucleotides will also embrace all chemically, enzymatically or metabolically modified forms of DNA or RNA, as well as the chemical forms of DNA and RNA characteristic of viruses.

The term "oligonucleotide" or "oligo" will refer short polynucleotides, typically between 10 to 40 bases in length.

"Polypeptide" as used herein refers to a molecule comprised of two or more amino acids joined to each other by peptide bonds or modified peptide bonds (i.e. isosteres). Amino acids include all 20 naturally gene-encoded amino acids as well as naturally or chemically modified amino acids. Polypeptides refer to both short chains of amino acids, commonly referred to as peptides, oligopeptides, or oligomers, and to longer chains, commonly referred to as proteins. Thus, "amino acid sequence" as used herein refers to an oligopeptide, peptide, polypeptide, or protein molecule and fragments or portions thereof, corresponding to a naturally occurring or synthetic molecule. Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule. Furthermore, polypeptides will also include amino acid sequences modified either by natural processes, such as post-translational processing, or by chemical modification techniques, which are well known in the art. A given polypeptide may contain many types of modifications or a given modification may be present in the same or varying degrees at several sites in a given polypeptide. Modifications can occur anywhere in the polypeptide, including but not limited to, the peptide backbone, the amino acid side-chains and the amino or carboxyl termini. All the above referred to modifications as well as their practice are well described in the research literature, both in basic texts and detailed monographs ("Proteins: Structure and Molecular Properties"; Creighton T E, Freeman W H, $2^{nd}$ Ed., New-York, 1993; "Posttranslational Covalent Modification of Proteins", Johnson B C, ed., Academic Press, New-York, 1983; Also: Seiter et al., Meth Enzymol 1990; 182: 626, and Rattan et al., Ann NY Acad Sci 1992; 663: 48).

"Peptide nucleic acid", as used herein, refers to a molecule which comprises an oligonucleotide to which an amino acid residue, such as lysine, and an amino group have been added. These small molecules, also designated anti-gene agents, stop transcript elongation by binding to their complementary strand of nucleic acid (Nielsen et al. Anticancer Drug Des 1993; 8: 53).

ASIC2A or ASIC3, as used herein, refers to the amino acid sequences of substantially purified ASIC2A and ASIC3 obtained preferably but not exclusively from human or rat, from any source whether natural, synthetic, semi-synthetic, or recombinant.

The term "variant" as used herein is a polynucleotide or polypeptide that differs from a reference polynucleotide or polypeptide, respectively. A typical variant of a polynucleotide differs in nucleotide sequence from another reference polynucleotide. Differences in the nucleotide sequence of the variant may or may not alter the amino acid sequence of a polypeptide encoded by the reference polynucleotide. Nucleotide changes may result in amino acid substitutions, additions, insertions, deletions, fusions, and truncations in the polypeptide encoded by the reference sequence, as discussed below. A typical variant of a polypeptide differs in amino acid sequence from another reference polypeptide. Generally, differences are such that the sequences of the reference polypeptide and the variant are closely similar overall and, in many regions, identical. A variant and reference polypeptide may differ in amino acid sequence by one or more substitutions, additions, insertions or deletions in any combination. A substituted or inserted amino acid residue may or may not be one encoded by the genetic code. A variant of a polynucleotide or polypeptide may be naturally occurring such as an allelic or a pseudoallelic variant, including polymorphisms or mutations at on or more bases, or it may be a variant that is not known to occur naturally. Non-naturally occurring variants of polynucleotides and polypeptides may be made by mutagenesis techniques or by direct synthesis. The term "mutant" are encompassed by the above definition of non-natural variants.

"splice variants" as referred to herein are variants, which result from the differential or alternative splicing and assembly of exons present in a given gene. Typically, the encoded proteins will display total identity in most regions, but lower identity in the specific region encoded by different exons.

A "deletion", as used herein, refers to a change in either amino acid or nucleotide sequence in which one or more amino acids or nucleotide residues, respectively, are absent, as compared to a reference polypeptide or polynucleotide.

An "insertion" or "addition", as used herein, refers to a change in an amino acid or nucleotide sequence resulting in the addition of one or more amino acid or nucleotide residues, respectively, as compared to a reference polypeptide or polynucleotide.

A "substitution", as used herein, refers to the replacement of one or more amino acids or nucleotides by different amino acids or nucleotides, respectively, as compared to a reference polypeptide or polynucleotide.

The term "derivative", as used herein, refers to the chemical modification of a nucleic acid encoding ASIC2A or ASIC3 or the encoded ASIC2A or ASIC3. Illustrative of such modifications would be replacement of hydrogen by an alkyl, acyl, or amino group. A nucleic acid derivative would encode a polypeptide which may or may not retain some or all of the essential biological characteristics of the natural molecule.

The term "identity" as used herein refers to a measure of the extent of identical nucleotides or amino acids that two or more polynucleotide or amino acid sequences have in common. In general, the sequences are aligned so that the highest order match is obtained, referred to as the "alignment". Such optimal alignments make use of gaps, which are inserted to maximize the number of matches using local homology algorithms, such as the Smith-Waterman alignment. The terms "identity", or "similarity", or "homology", or "alignment" are well known to skilled artisans and methods to perform alignments and measure identity are widely described and taught in the literature: Dayhoff et al., Meth Enzymol 1983; 91: 524—Lipman D J and Pearson W R, Science 1985; 227: 1435—Altschul et al., J Mol Biol 1990; 215: 403.—Pearson W R, Genomics 1991; 11: 635.—Gribskov M and Devreux J, eds. (1992) Sequence Analysis Primer, W H Freeman & Cie, New-York.—Altschul et al., Nature Gen 1994; 6: 119. Furthermore, methods to perform alignments and to determine identity and similarity are codified in computer programs and software packages, some of which may also be web-based and accessible on the internet. Preferred software include but are not limited to BLAST (Basic Local Alignment Search Tools), including Blastn, Blastp, Blastx, tBlastn (Altschul et al., J Mol Biol 1990; 215: 403), FastA and TfastA (Pearson and Lipman, PNAS 1988; 85: 2444), Lasergene99 (DNASTAR, Madison Wis.), Omiga 2.0 or MacVector (Oxford Molecular Group, Cambridge, UK), Wisconsin Package (Genetic Computer Group (GCG), Madison, Wis.), Vector NTI Suite (InforMax Inc., N. Bethesta, Md.), GeneJockey II (Biosoft, Cambridge, UK).

As an illustration, by a polynucleotide having a nucleotide sequence with at least, for example, 95% "identity" to a reference nucleotide sequence of SEQ ID NO: 1, is intended that the nucleotide sequence of the polynucleotide is identical to the reference sequence except that the polynucleotide sequence may include up to five point mutations, or divergent nucleotides, per 100 nucleotides of the reference nucleotide sequence of SEQ ID NO: 1. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more continuous groups within the reference sequence.

Similarly, by a polypeptide having an amino acid sequence having at least, for example, 95% "identity" to a reference amino acid sequence of SEQ ID NO: 2, is intended that the amino acid sequece of the polypeptide is identical to the reference sequence except that the polypeptide sequence may include up to five amino acid alterations per each 100 amino acids of the reference amino acid sequence of SEQ ID NO: 2. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence, or anywhere between those terminal positions, interspersed either individually among residues in the reference sequence or in one or more continuous groups within the reference sequence.

The term "biologically active" or "biological activity", as used herein, refer to a protein having structural, regulatory, biochemical, electrophysiological or cellular functions of a naturally occurring molecule. Likewise, "immunologically active" refers to the capability of the natural, recombinant, or synthetic ASIC2A, or ASIC3, or ASIC-2S.2, or any oligopeptide thereof, to induce a specific immune response in appropriate animals or cells and to bind with specific antibodies.

As used herein, "specific antibodies" "antibodies to ASIC-2S.2" and "ASIC-2S.2-specific antibodies" refer to antibodies which specifically bind the ASIC-2S.2 protein complex, or specifically bind ASIC2A and/or ASIC3 in their heteromultimeric conformation, or antibodies specifically binding ASIC2A or ASIC3 and capable of inhibiting, preventing or disrupting the interaction, association or assembly between ASIC2A and ASIC3, as described herein.

As used herein, "proton-gated" and "acid-sensing" refer to an increase in cation permeability of a channel molecule induced by an increase in proton ion concentration, also described as increased acidity or lowering of pH.

As used herein, "gain of function" refers to a potentiation of an existing biological activity and/or an acquisition of a novel biological activity. Similarly, "Loss of function" refers to a partial or complete loss of one or more existing biological activities. The expression "Dominant-negative" refers to a loss-of-function derivative of ASIC2A or ASIC3, which when coexpressed with a fully functional ASIC2A or ASIC3, in vivo, for example as a transgene, or in vitro, for example in an assay used to test the specific biological activity (for example "acid-sensing"), will dominate the response and impose the loss of biological activity on all other ASIC subunits associated with it.

The term "agonist", as used herein, refers to a molecule, which causes a change in ASIC-2S.2 and modulates or induces directly or indirectly a biological activity of the ASIC-2S.2 heteromultimeric channels. Agonists may include proteins, nucleic acids, aptamers, carbohydrates, or any other molecules, which display the properties described herein above.

The terms "antagonist" or "inhibitor", as used herein, refer to a molecule which modulates or blocks directly or indirectly a biological activity of the ASIC-2S.2 heteromultimeric channels. Antagonists and inhibitors may include proteins, nucleic acids, aptamers, carbohydrates, or any other molecules which display the properties described herein above.

The term "modulate", as used herein, refers to a change or an alteration in the biological activity of ASIC-2S.2 heteromultimeric channels. Modulation may be an increase or a decrease in protein activity, a change in binding characteristics, or any other change in the biological, functional or immunological properties of the ASIC-2S.2.

The term "mimetic", as used herein, refers to a molecule, the structure of which is developed from knowledge of the structure of ASIC2A or ASIC3 or portions thereof and, as such, is able to effect some or all of the actions of ASIC-like molecules.

The term "substantially purified", as used herein, refers to nucleic or amino acid sequences that are removed from their natural environment, isolated or separated, and are at least 60% free, preferably 75% free, more preferably 90%, even more preferable 95%, and most preferably 99% free from other components with which they are naturally associated.

"Amplification" as used herein refers to the production of additional copies of a nucleic acid and is generally carried out using polymerase chain reaction (PCR) technologies well known in the art ("PCR Primer: a laboratory manual" Dieffenbach C W and Dveksler G S, eds., 1995, CSHL Press, Plainview, N.Y.).

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., RNAse Protection Assay analysis) or between one nucleic acid sequence present in solution and another nucleic acid sequence immobilized on a solid support (e.g., membranes, filters, chips, pins or glass slides to which cells have been fixed for in situ hybridization).

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single-stranded molecules. The degree of complementarity between nucleic acid strands has significant effects on the efficiency and strength of hybridization between nucleic acid strands. This is of particular importance in amplification reactions, which depend upon binding between nucleic acid strands.

The term "homology", as used herein, refers to a degree of complementarity. There may be partial homology or complete homology (i.e., identity). A partially complementary sequence is one that at least partially inhibits an identical sequence from hybridizing to a target nucleic acid; it is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding, the probe will not hybridize to the second non-complementary target sequence.

As known in the art, numerous equivalent conditions may be employed to comprise either low or high stringency conditions. Factors such as the length and nature (DNA, RNA, base composition) of the sequence, nature of the target (DNA, RNA, base composition, presence in solution or immobilization, etc.), and the concentration of the salts and other components (e.g., the presence or absence of formamide, dextran sulfate and/or polyethylene glycol) are considered and the hybridization solution may be varied to generate conditions of either low or high stringency different from, but equivalent to, the above listed conditions.

The term "stringent conditions", as used herein, is the "stringency" which occurs within a range from about Tm-5° C. (5° C. below the melting temperature (Tm) of the probe) to about 20° C. to 25° C. below Tm. As will be understood by those of skill in the art, the stringency of hybridization may be altered in order to identify or detect identical or related polynucleotide sequences.

The term "antisense", as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter, which permits the synthesis of a complementary strand. Once introduced into a cell, this transcribed strand combines with natural sequences produced by the cell to form duplexes. These duplexes then block either the further transcription or translation. In this manner, mutant phenotypes may be generated. The designation "negative" is sometimes used in reference to the antisense strand, and "positive" is sometimes used in reference to the sense strand.

The term "portion", as used herein, with regard to a protein (as in "a portion of a given protein") refers to fragments of that protein. The fragments may range in size from four amino acid residues to the entire amino acid sequence minus one amino acid. Thus, a protein "comprising at least a portion of the amino acid sequence of SEQ ID NO:2" encompasses the full-length human ASIC2A and fragments thereof.

"Transformation" or "transfection", as defined herein, describes a process by which exogenous DNA enters and changes a recipient cell. It may occur under natural or artificial conditions using various methods well known in the art. Transformation or transfection may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" or "transfected" cells include stably transformed cells in which the inserted DNA is capable of replication either as an autonomously replicating plasmid or as part of the host chromosome. They also include cells that transiently express the inserted DNA or RNA for limited periods of time.

The term "antigenic determinant", as used herein, refers to that portion of a molecule that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The terms "specific binding" or "specifically binding", as used herein, in reference to the interaction of an antibody and a protein or peptide, mean that the interaction is dependent upon the presence of a particular structure (i.e., the antigenic determinant or epitope) on the protein; in other words, the antibody is recognizing and binding to a specific protein structure rather than to proteins in general. For example, if an antibody is specific for epitope "A", the presence of a protein containing epitope A (or free, unlabeled A) in a reaction containing labeled "A" and the antibody will reduce the amount of labeled A bound to the antibody.

The term "sample", as used herein, is used in its broadest sense. A biological sample suspected of containing nucleic acids encoding ASIC2A and ASIC3 or fragments thereof may comprise a cell, chromosomes isolated from a cell (e.g., a spread of metaphase chromosomes), genomic DNA (in solution or bound to a solid support such as for Southern analysis), RNA (in solution or bound to a solid support such as for northern analysis), cDNA (in solution or bound to a solid support), an extract from cells or a tissue, and the like.

The term "correlates with expression of a polynucleotide", as used herein, indicates that the detection by northern analysis and/or RT-PCR of the presence of ribonucleic acid that is related to SEQ ID NO:1, SEQ ID NO:3, SEQ ID NO:5 or SEQ ID NO:7 is indicative of the presence of mRNA encoding, respectively, hASIC2A, hASIC3, rASIC2A or rASIC3 in a sample and thereby correlates with expression of the transcript encoding the protein.

"Alterations" in the polynucleotides of SEQ ID NO:1, SEQ ID NO:3, SEQ ID NO:5 or SEQ ID NO:7, as used herein, comprise any alteration in the sequence of polynucleotides encoding, respectively, hASIC2A, hASIC3, rASIC2A or rASIC3, including deletions, insertions, and point mutations that may be detected using hybridization assays. Included within this definition is the detection of alterations to the genomic DNA sequence which encodes hASIC2A, hASIC3, rASIC2A or rASIC3 (e.g., by alterations in the pattern of restriction fragment length polymorphisms capable of hybridizing to SEQ ID NO:1, SEQ ID NO:3, SEQ ID NO:5 or SEQ ID NO:7), the inability of a selected fragment of SEQ ID NO:1, SEQ ID NO:3, SEQ ID NO:5 or SEQ ID NO:7 to hybridize to a sample of genomic DNA (e.g., using allele-specific oligonucleotide probes), and improper or unexpected hybridization, such as hybridization to a locus other than the normal chromosomal locus for the polynucleotide sequence encoding hASIC2A, hASIC3, rASIC2A or rASIC3 (e.g., using fluorescent in situ hybridization (FISH) to metaphase chromosome spreads).

As used herein, the term "antibody" refers to intact molecules as well as fragments thereof, such as Fa, $F(ab')_2$, and Fv, which are capable of binding the epitopic determinant.

Antibodies that bind hASIC2A, hASIC3, rASIC2A or rASIC3 polypeptides can be prepared using intact polypeptides or fragments containing small peptides of interest as the immunizing antigen. The polypeptide or peptide used to immunize an animal can be derived from translated RNA or synthesized chemically, and can be conjugated to a carrier protein, if desired. Commonly used carriers that are chemically coupled to peptides include bovine serum albumin and thyroglobulin. The coupled peptide is then used to immunize the animal (e.g., a mouse, a rat or a rabbit). These methods are well described in the literature: e.g. "Antibodies: A Laboratory Manual", Harlow E and Lane D, eds., 1998, CSHL Press, Plainview, N.Y.).

The term "humanized antibody", as used herein, refers to antibody molecules in which amino acids have been replaced in the non-antigen binding regions in order to more closely resemble a human antibody, while still retaining the original binding ability.

DISCLOSURE OF THE INVENTION

The present invention is based on the discovery of a novel Acid Sensing Ion Channel (ASIC) with distinctive channel properties and biological activity. This novel channel, ASIC-2S.2 is a heteromultimeric complex comprised of two different types of ASIC subunits, namely ASIC2A and ASIC3 (see FIG. 8). The present invention is also based on the discovery of a new use of polynucleotides encoding ASIC2A and ASIC3, said use being the inclusion of ASIC2A and ASIC3 in the assembly of a heteromultimeric ion channel. This invention further includes the use of the above compositions for diagnosis, prevention, or treatment of diseases related to the expression of the heteromultimeric ASIC channel disclosed herein. The preferred polynucleotides are those of SEQ ID NO:1, SEQ ID NO:3, SEQ ID NO:5 and SEQ ID NO:7, encoding, respectively, the hASIC2A, hASIC3, rASIC2A and rASIC3 of SEQ ID NO:2, SEQ ID NO:4, SEQ ID NO:6 and SEQ ID NO:8. The above enumerated polynucleotides have already been embodied in the following patents or patent applications: U.S. Pat. No. 5,892,018; WO9835034; WO9921981; WO9854316. The general notion of heteromultimeric associations between subunits of the same family is widely recognized by those skilled in the art. The inventive step resides in finding the functional combinations of known subunits as well as the changes in channel properties and/or biological activity. Patent application WO9835034 does indeed claim hybrid ASIC channels but supports this claim with indirect evidence suggesting interactions between ASIC and MDEG1, MDEG1 and MDEG2, and between MDEG2 and DRASIC (see above). The present invention demonstrates for the first time the direct biochemical interaction between two distinct ASIC subunits, namely ASIC2A and ASIC3, which produces a novel proton-gated ion channel with distinctive properties.

The invention also encompasses heteromultimeric ASIC channels comprised of ASIC2A and/or ASIC3 variants, in any possible combination of wild-type and variant forms. A preferred ASIC2A variant is one having at least 80%, and more preferably 90%, amino acid sequence identity to the ASIC2A amino acid sequence of SEQ ID NO: 2 or SEQ ID NO.6. A most preferred ASIC2A variant is one having at least 95% amino acid sequence identity to SEQ ID NO: 2 or SEQ ID NO:6, while those with 97-99% amino acid sequence identity are most highly preferred. A preferred ASIC3 variant is one having at least 80%, and more preferably 90%, amino acid sequence identity to the ASIC3 amino acid sequence of SEQ ID NO:4 or SEQ ID NO.8. A most preferred ASIC3 variant is one having at least 95% amino acid sequence identity to SEQ ID NO:4 or SEQ ID NO:8, while those with 97-99% amino acid sequence identity are most highly preferred.

The invention also encompasses polynucleotides which encode ASIC2A or ASIC3 polypeptides. Accordingly, any nucleic acid sequence, which encodes the amino acid sequence of ASIC2A or ASIC3 can be used to generate recombinant molecules which express ASIC2A or ASIC3. In a particular embodiment, the invention encompasses the polynucleotide comprising the nucleic acid of SEQ ID NO: 1, SEQ ID NO:3, SEQ ID NO: 5, and SEQ ID NO:7.

It will be appreciated by those skilled in the art that as a result of the degeneracy of the genetic code, a multitude of nucleotide sequences encoding ASIC2A or ASIC3, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring ASIC2A or ASIC3, and all such variations are to be considered as being specifically encompassed.

Although nucleotide sequences which encode ASIC2A or ASIC3 and their variants are preferably capable of hybridizing to the nucleotide sequence of the naturally occurring ASIC2A or ASIC3 under appropriately selected conditions of stringency, it may be advantageous to produce nucleotide sequences encoding ASIC2A or ASIC3 or their derivatives possessing a substantially different or non-naturally occurring codon usage. Codons may be selected to increase the rate at which expression of the peptide occurs in a particular prokaryotic or eukaryotic expression host in accordance with the frequency with which particular codons are utilized by the host. Other reasons for substantially altering the nucleotide sequence encoding ASIC2A or ASIC3 and their derivatives without altering the encoded amino acid sequences include the production of RNA transcripts having more desirable properties, such as a greater half-life, than transcripts produced from the naturally occurring sequence.

The invention also encompasses production of a DNA sequence, or portions thereof, which encode ASIC2A or ASIC3 and their derivatives, entirely by synthetic chemistry. After production, the synthetic gene may be inserted into any of the many available DNA vectors and cell systems using reagents that are well known in the art at the time of the filing of this application. Moreover, synthetic chemistry may be used to introduce mutations into a sequence encoding ASIC2A or ASIC3 or any portion thereof.

Further encompassed by the invention are polynucleotide sequences that are capable of hybridizing to the claimed nucleotide sequences, and in particular, to those shown in SEQ ID NO: 1, SEQ ID NO:3, SEQ ID NO: 5, and SEQ ID NO:7, under various conditions of stringency. Hybridization conditions are based on the melting temperature (Tm) of the nucleic acid binding complex or probe, as taught in Berger and Kimmel (Meth Enzymol 1987: 152), and may be used at a defined stringency. Excluded from the above defined polynucleotides are polynucleotides disclosed in Patent Application WO9835034 under SEQ ID NO:1, SEQ ID NO:2, and SEQ ID NO:6.

Altered nucleic acid sequences encoding ASIC2A or ASIC3 which are encompassed by the invention include deletions, insertions, or substitutions of different nucleotides resulting in a polynucleotide that encodes the same or a functionally equivalent ASIC2A or ASIC3. The encoded protein may also contain deletions, insertions, or substitutions of amino acid residues, which result in a functionally equivalent ASIC2A or ASIC3. Also encompassed by the invention are altered nucleic acid sequences, including deletions, insertions or substitutions, which result in a polynucleotide that encodes an ASIC2A or ASIC3 polypeptide with increased or novel biological activity ("gain of function"), or an ASIC2A or ASIC3 polypeptide with decreased or suppressed biological activity ("Loss of function" or "Dominant-negative"). The encoded protein may also contain deletions, insertions, or substitutions of amino acid residues, which result in a functionally divergent ASIC2A or ASIC3, as described herein above. Deliberate amino acid substitutions may be made on the basis of similarity in polarity, charge, solubility, hydrophobicity, hydrophilicity, and/or the amphipathic nature of the residues as long as the biological activity of ASIC2A or ASIC3 is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine; phenylalanine and tyrosine.

Also included within the scope of the present invention are alleles of the genes encoding ASIC2A or ASIC3. As used herein, an "allele" or "allelic sequence" is an alternative form of the gene, which may result from at least one mutation in the nucleic acid sequence. Alleles may result in altered mRNAs or polypeptides whose structure or function may or may not be altered. Any given gene may have none, one, or many allelic forms. Common mutational changes, which give rise to alleles, are generally ascribed to natural deletions, additions, or substitutions of nucleotides. Each of these types of changes may occur alone, or in combination with the others, one or more times in a given sequence.

Methods for DNA sequencing, which are well known and generally available in the art, may be used to practice any embodiments of the invention. The methods may employ such enzymes as the Klenow fragment of DNA polymerase I, Sequenase II (US Biochemical Corp, Cleveland, Ohio), Taq polymerase (Perkin Elmer), thermostable T7 polymerase (Amersham, Chicago, Ill.), or combinations of recombinant polymerases and proofreading exonucleases such as the ELONGASE Amplification System marketed by Gibco BRL (Gaithersburg, Md.) or the EXPAND High fidelity or Long-Template systems (Roche). Preferably, the process is automated with machines such as the Hamilton Micro Lab 2200 (Hamilton, Reno, Nev.), Peltier Thermal Cycler (PTC200; M.J. Research, Watertown, Mass.) and the ABI 377 DNA sequencers (Perkin Elmer), to name a few.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled devise camera. Output/light intensity may be converted to electrical signal using appropriate software (e.g. Genotyper™ and Sequence Navigator™, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

The nucleotide sequences of the present invention can be engineered using methods generally known in the art in order to alter the ASIC2A or ASIC3 coding sequence for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequence. For example, site-directed mutagenesis may be used to insert new restriction sites, to alter glycosylation patterns, to change codon preference, to produce splice variants, or other mutations, and so forth. Alternatively, the nucleotide sequences can be engineered to generate chimeric ASIC2A or ASIC3 channels, where portions of the ASIC2A channel are substituted with equivalent portions of the ASIC3 subunit and/or vice versa. Chimeric ASIC2A or ASIC3 can also be constructed by substituting portions ASIC2A or ASIC3 with equivalent portions from other ASIC subunits, for example the ASIC1A or ASIC4. Nucleic acids can also be engineered to encode as a single polypeptide two or more ASIC2A and/or ASIC3 subunits in tandem.

In another embodiment of the invention, a natural, modified, or recombinant polynucleotide encoding ASIC2A or ASIC3 may be ligated to a heterologous sequence to encode a fusion protein. For example, to provide biochemical evidence of direct protein-protein interactions between ASIC2A and ASIC3, polynucleotides encoding ASIC2A and ASIC3 are modified to encode chimeric ASIC2A or ASIC3 proteins with N- or C-terminal extensions adding a foreign epitope recognised by commercially available antibodies or affinity resins. A fusion protein may also be engineered to contain a cleavage site located between the ASIC2A or ASIC3 encoding sequence and the heterologous protein sequence, so that ASIC2A or ASIC3 may be cleaved and purified away from the heterologous moiety.

In another embodiment, the coding sequence of ASIC2A and/or ASIC3 may be synthesized, in whole or in part, using chemical methods well known in the art (see Caruthers et al., Nuc. Acids Res. Symp. Ser. 1980; 215-23; Horn et al., Nuc. Acids Res. Symp. Ser. 1980; 225-232). Alternatively, the protein itself may be produced using chemical methods to synthesize the ASIC2A and/or ASIC3 amino acid sequence, or a portion thereof. For example, peptide synthesis can be performed using various solid-phase techniques (Roberge et al., Science 1995; 269: 202) and automated synthesis may be achieved, for example, using the ABI 431A Peptide Synthesizer (Perkin Elmer).

The newly synthesized peptide may be substantially purified by preparative high performance liquid chromatography (e.g., Creighton T. (1983) "Proteins, Structures and Molecular Principles", W. H. Freeman & Co., New York, N.Y.). The composition of the synthetic peptides may be confirmed by amino acid analysis or sequencing (e.g., the Edman degradation procedure; Creighton T (1983), supra). Additionally, the amino acid sequence of ASIC2A and/or ASIC3, or any part thereof, may be altered during direct synthesis and/or combined using chemical methods with sequences from other proteins, or any part thereof, to produce a variant polypeptide.

In order to express a biologically active ASIC2A and/or ASIC3, the nucleotide sequence encoding ASIC2A and/or ASIC3 or functional equivalents thereof, may be inserted into an appropriate expression vector, i.e., a vector, which contains the necessary elements for the transcription and translation of the inserted coding sequence.

Methods which are well known to those skilled in the art may be used to construct expression vectors containing a ASIC2A and/or ASIC3 coding sequences and appropriate transcriptional and translational control elements. These methods include in vitro recombinant DNA techniques, synthetic techniques, and in vivo genetic recombination. Such techniques are described in "Molecular Cloning: A Laboratory Manual", Sambrook J, Ed., CSHL Press, 1989, Cold Spring Harbor, N.Y., and "Current Protocols in Molecular Biology", Ausubel et al., John Wiley & Sons, 1989, New York, N.Y.

A variety of expression vector/host systems may be utilized to contain and express ASIC2A and/or ASIC3 coding sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the Bluescript® phagemid (Stratagene, La Jolla, Calif.) or pSport1™ plasmid (Gibco BRL) and ptrp-lac hybrids, and the like may be used. Other preferred prokaryotic vectors include but are not limited to pQE-9, pQE60, pQE70 (Quiagen), pNH8A, pNH16a, pNH18a, pNH46A (Stratagene) ptrc99a, pKK223-3, pKK233-3, pDR540, pRIT5 (Pharmacia). The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding ASIC2A and/or ASIC3, vectors based on SV40 or EBV may be used with an appropriate selectable marker.

In bacterial systems, a number of expression vectors may be selected depending upon the use intended for ASIC2A and/or ASIC3. For example, when large quantities of ASIC2A and/or ASIC3 are needed for the induction of antibodies, vectors, which direct high level expression of fusion proteins that are readily purified, may be used. Such vectors include, but are not limited to, the multifunctional E. coli cloning and expression vectors such as Bluescript® (Stratagene, La Jolla, Calif.), into which the sequence encoding ASIC2A or ASIC3 may be ligated in frame with sequences for the amino-terminal Methionine and the subsequent 7 residues of β-galactosidase so that a hybrid protein is produced; pIN vectors (Van Heeke and Schuster, J. Biol. Chem. 1989; 264: 5503); and the like; pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In addition to bacteria, eucaryotic microbes, such as yeast, may also be used as hosts. Laboratory strains of Saccharomyces cerevisiae, Baker's yeast, are most used although a number of other strains or species are commonly available. Vectors employing, for example, the 2μ origin of replication of Broach et al. (Meth Enzymol 1983; 101: 307), or other yeast compatible origins of replication (see, for example, Stinchcomb et al. Nature 1979: 282; 39, Tschumper et al., Gene 1980: 10; 157, Clarke et al., Meth Enzymol 1983; 101: 300) may be used. Control sequences for yeast vectors include promoters for the synthesis of glycolytic enzymes (Hess et al. J Adv Enzyme Reg 1968; 7: 149; Holland et al., Biochemistry 1978; 17: 4900). Additional promoters known in the art include the promoter for 3-phosphoglycerate kinase (Hitzeman et al., J Biol Chem 1980; 255: 2073), alcohol oxidase, and PGH. Other promoters, which have the additional advantage of transcription controlled by growth conditions and/or genetic background are the promoter regions for alcohol dehydrogenase 2, isocytochrome C, acid phosphatase, degradative enzymes associated with nitrogen metabolism, the alpha-factor system and enzymes responsible for maltose and galactose utilization. It is also believed terminator sequences are desirable at the 3' end of the coding sequences. Such terminators are found in the 3' untranslated region following the coding sequences in yeast-derived genes. For reviews, see "Current Protocols in Molecular Biology", Ausubel et al., John Wiley & Sons, 1989, New York, N.Y. and Grant et al., Meth Enzymol. 1987; 153: 516.

In cases where plant expression vectors are used, the expression of a sequence encoding ASIC2A or ASIC3 may be driven by any of a number of promoters. For example, viral promoters such as the 35S and 19S promoters of CaMV may be used alone or in combination with the omega leader sequence from TMV (Takamatsu et al., EMBO J. 1987; 6: 307; Brisson et al., Nature 1984; 310: 511). Alternatively, plant promoters such as the small subunit of RUBISCO or heat shock promoters may be used (Coruzzi et al., EMBO J. 1984; 3: 1671; Broglie et al., Science 1984; 224: 838; Winter et al., Results Probl. Cell Differ 1991; 17: 85). These constructs can be introduced into plant cells by direct DNA transformation or pathogen-mediated transfection. Such techniques are described in a number of generally available reviews (see, for example, Hobbs S or Murry L E in "McGraw Hill Yearbook of Science and Technology" McGraw Hill, 1992, New York, N.Y.; pp. 191-196 or Weissbach and Weissbach in "Methods for Plant Molecular Biology", Academic Press, 1988, New York, N.Y.; pp. 421-463).

An insect system may also be used to express ASIC2A and/or ASIC3. For example, in one such system, Autographa californica nuclear polyhedrosis virus (AcNPV) is used as a vector to express foreign genes in Spodoptera frugiperda cells or in Trichoplusia larvae. The sequence encoding ASIC2A and/or ASIC3 may be cloned into a non-essential region of the virus, such as the polyhedrin gene, and placed under control of the polyhedrin promoter. Successful insertion of ASIC2A or ASIC3 will render the polyhedrin gene inactive and produce recombinant virus lacking coat protein. The recombinant viruses may then be used to infect, for example, S. frugiperda cells or Trichoplusia larvae in which ASIC2A and/or ASIC3 may be expressed (Smith et al., J Virol 1983; 46: 584; Engelhard et al., Proc Natl Acad Sci 1994; 91: 3224).

In mammalian host cells, a number of viral-based expression systems may be utilized. In cases where an adenovirus is used as an expression vector, a sequence encoding ASIC2A and/or ASIC3 may be ligated into an adenovirus transcription/translation complex consisting of the late promoter and tripartite leader sequence. Insertion in a non-essential E1 or E3 region of the viral genome may be used to obtain a viable virus, which is capable of expressing ASIC2A and/or ASIC3 in infected host cells (Logan and Shenk, Proc Natl Acad Sci 1984; 81: 3655). In addition, transcription enhancers, such as the Rous sarcoma virus (RSV) enhancer, may be used to increase expression in mammalian host cells.

Specific initiation signals may also be used to achieve more efficient translation of a sequence encoding ASIC2A and/or ASIC3. Such signals include the ATG initiation codon and adjacent sequences. In cases where sequences encoding ASIC2A or ASIC3, together with their initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure the correct translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf et al., Results Probl Cell Differ 1994; 20: 125; Bittner et al., Meth Enzymol 1987; 153: 516).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, WI38, and COS, which have specific cellular machinery and characteristic mechanisms for such post-translational activities, may be chosen to ensure the correct modification and processing of the foreign protein.

In a preferred expression system, cDNAs or cRNAs encoding ASIC2A and/or ASIC3 are coinjected directly into *Xenopus* oocytes, cDNAs into nuclei and cRNA into the cytoplasm, thereby allowing for in vitro translation and assembly into a functional heteromultimeric proton-gated channel capable of demonstrating functional characteristics of native proton-gated channels including ion selectivity, gating-kinetics, ligand preferences, and sensitivity to pharmacological agents such as amiloride for a model assay which mimics in vivo characteristics.

For long-term, high-yield production of recombinant proteins, stable expression is preferred. For example, cell lines, which stably express ASIC2A or ASIC3, or both ASIC2A and ASIC3, may be transformed using expression vectors which may contain viral origins of replication and/or endogenous expression elements and a selectable marker gene on the same or separate vector. Following the introduction of the vector, cells may be allowed to grow for 1-2 days in an enriched media before they are switched to selective media. The purpose of the selectable marker is to confer resistance to selection, and its presence allows growth and recovery of cells, which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler et al., Cell 1977; 11: 223) and adenine phospho-ribosyltransferase (Lowy et al., Cell 1980; 22: 817) genes which can be employed in tk+- or aprt+-cells, respectively. Also, antimetabolite, antibiotic, or herbicide resistance can be used as the basis for selection; for example, dhfr, which confers resistance to methotrexate (Wigler et al., Proc Natl Acad Sci 1980; 77: 3567); npt, which confers resistance to the aminoglycosides neomycin and G-418 (Colbere-Garapin et al., J Mol Biol 1981; 150: 1) and als or pat, which confer resistance to chlorsulfuron and phosphinotricin acetyltransferase, respectively (Murry L E, supra). Additional selectable genes have been described, for example, trpB, which allows cells to utilize indole in place of tryptophan, or hisD, which allows cells to utilize histinol in place of histidine (Hartman and Mulligan, Proc Natl Acad Sci 1988; 85: 8047). Recently, the use of visible markers has gained popularity with such markers as anthocyanins, β-glucuronidase and its substrate GUS, and luciferase and its substrate luciferin, being widely used not only to identify transformants, but also to quantify the amount of transient or stable protein expression attributable to a specific vector system (Rhodes et al., Methods Mol Biol 1995; 55: 121).

Although the presence/absence of marker for gene expression suggests that the gene of interest is also present, its presence and expression may need to be confirmed. For example, if the sequence encoding ASIC2A and/or ASIC3 is inserted within a marker gene sequence, recombinant cells containing sequences encoding ASIC2A and/or ASIC3 can be identified by the absence of marker gene function. Alternatively, a marker gene can be placed in tandem with a sequence encoding ASIC2A or ASIC3 under the control of a single promoter. Expression of the marker gene in response to induction or selection usually indicates expression of the tandem gene as well.

Alternatively, host cells, which contain the coding sequences for ASIC2A and/or ASIC3 and express both ASIC2A and ASIC3 may be identified by a variety of procedures known to those of skill in the art. These procedures include, but are not limited to, DNA-DNA or DNA-RNA hybridizations and protein bioassay or immunoassay techniques, which include membrane, solution, or chip based technologies for the detection and/or quantification of the nucleic acid or protein.

The presence of the polynucleotide sequences encoding ASIC2A and/or ASIC3 can be detected by DNA-DNA or DNA-RNA hybridization or amplification using probes or portions or fragments of polynucleotides encoding ASIC2A or ASIC3. Nucleic acid amplification based assays involve the use of oligonucleotides or oligomers based on the ASIC2A- or ASIC3-encoding sequences to detect transformants containing DNA or RNA encoding ASIC2A and/or ASIC3. As used herein "oligonucleotides" or "oligomers" refer to a nucleic acid sequence of at least about 10 nucleotides and as many as about 60 nucleotides, preferably about 15 to 30 nucleotides, and more preferably about 20-25 nucleotides, which can be used as a probe or amplimer.

A variety of protocols for detecting and measuring the co-expression of ASIC2A and ASIC3, using either polyclonal or monoclonal antibodies specific for each protein are known in the art. Examples include enzyme-linked immunosorbent assay (ELISA), radioimmunoassay (RIA), and fluorescent activated cell sorting (FACS). A two-site, monoclonal-based immunoassay utilizing monoclonal antibodies reactive to two non-interfering epitopes on ASIC2A or ASIC3 is preferred, but a competitive binding assay may be employed. These and other assays are described, among other places, in "Serological Methods: A Laboratory Manual", Hampton et al., APS Press, 1990, St-Paul, Mich. and Maddox et al., J Exp Med 1983; 158: 1211).

A wide variety of labels and conjugation techniques are known by those skilled in the art and may be used in various nucleic acid and amino acid assays. Means for producing labeled hybridization or PCR probes for detecting sequences related to polynucleotides encoding ASIC2A or ASIC3 include oligo-labeling, nick translation, end-labeling or PCR amplification using a labeled nucleotide. Alternatively, the sequence encoding ASIC2A or ASIC3, or any portion thereof, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides. These procedures may be conducted using a variety of commercially available kits: from e.g. Pharmacia & Upjohn, (Kalamazoo, Mich.); Promega (Madison Wis.); and U.S. Biochemical Corp. (Cleveland, Ohio), or Ambion (Austin, Tex.). Suitable reporter molecules or labels, which may be used, include radionuclides, enzymes, fluorescent, chemiluminescent, or chromogenic agents as well as substrates, cofactors, inhibitors, magnetic particles, and the like.

Host cells co-transformed with nucleotide sequences encoding both ASIC2A and/or ASIC3 may be cultured under conditions suitable for the expression and recovery of the proteins from cell culture. The proteins produced by a recombinant cell may be secreted or contained intracellularly depending on the sequence and/or the vector used. As will be understood by those of skill in the art, expression vectors containing polynucleotides, which encode ASIC2A or ASIC3 may be designed to contain signal sequences which direct secretion of ASIC2A and/or ASIC3 through a prokaryotic or eukaryotic cell membrane.

Other recombinant constructions may be used to join sequences encoding ASIC2A or ASIC3 to nucleotide sequence encoding a polypeptide domain, which will facilitate purification of the expressed proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and ASIC2A or ASIC3 may be used to facilitate purification. One such expression vector provides for expression of a fusion protein containing ASIC2A and/or ASIC3, a thioredoxin or an enterokinase cleavage site, and followed by six histidine residues. The histidine residues facilitate purification on IMIAC (immobilized metal ion affinity chromatography as described in Porath et al., Prot Exp Purif 1992; 3: 263) while the enterokinase cleavage site provides a means for purifying ASIC2A or ASIC3 from the fusion protein. A discussion of vectors which contain fusion proteins is provided in Kroll et al. (DNA Cell Biol 1993; 12: 441).

In addition to recombinant production, fragments of ASIC2A and/or ASIC3 may be produced by direct peptide synthesis using solid-phase techniques (see Stewart et al., "Solid-Phase Peptide Synthesis", W H Freeman & Co., 1969, San Francisco, Calif.; Merrifield et al., J Am Chem Soc 1963; 85: 2149). Chemical synthesis may be performed using manual techniques or by automation. Automated synthesis may be achieved, for example, using Applied Biosystems 431A Peptide Synthesizer (Perkin Elmer). Various fragments of ASIC2A and/or ASIC3 may be chemically synthesized separately and combined using chemical methods to produce the full-length molecule.

Thus as set forth herein the invention includes the provision of a novel subfamily of heteromultimeric proton-gated ion channels as exemplified by the novel association of ASIC2A and ASIC3 polypeptides, encoded, respectively, by nucleic acids of SEQ ID NO: 1 or NO:5 and SEQ ID NO: 3 or NO:7 as well as DNA sequences which hybridize thereto under stringent hybridization conditions, and DNA sequences encoding the same allelic variant or analogue proton-gated channel protein through use of at least in part degenerate codons. The ASIC-2S.2 channel complex can also be used to located and identify other closely related members of this subfamily as described in Cannessa et al (Nature 1994; 367: 463).

Polypeptides of SEQ ID NO:2, NO:4, NO:6 and NO:8, as well as any protein, protein fragment, synthetic protein or peptide thereof are projected to have uses earlier described including therapeutic, diagnostic, and prognostic assays and protocols and will provide the basis for monoclonal and polyclonal antibodies specifically reactive with the channel protein.

Therapeutics

Figure 4:
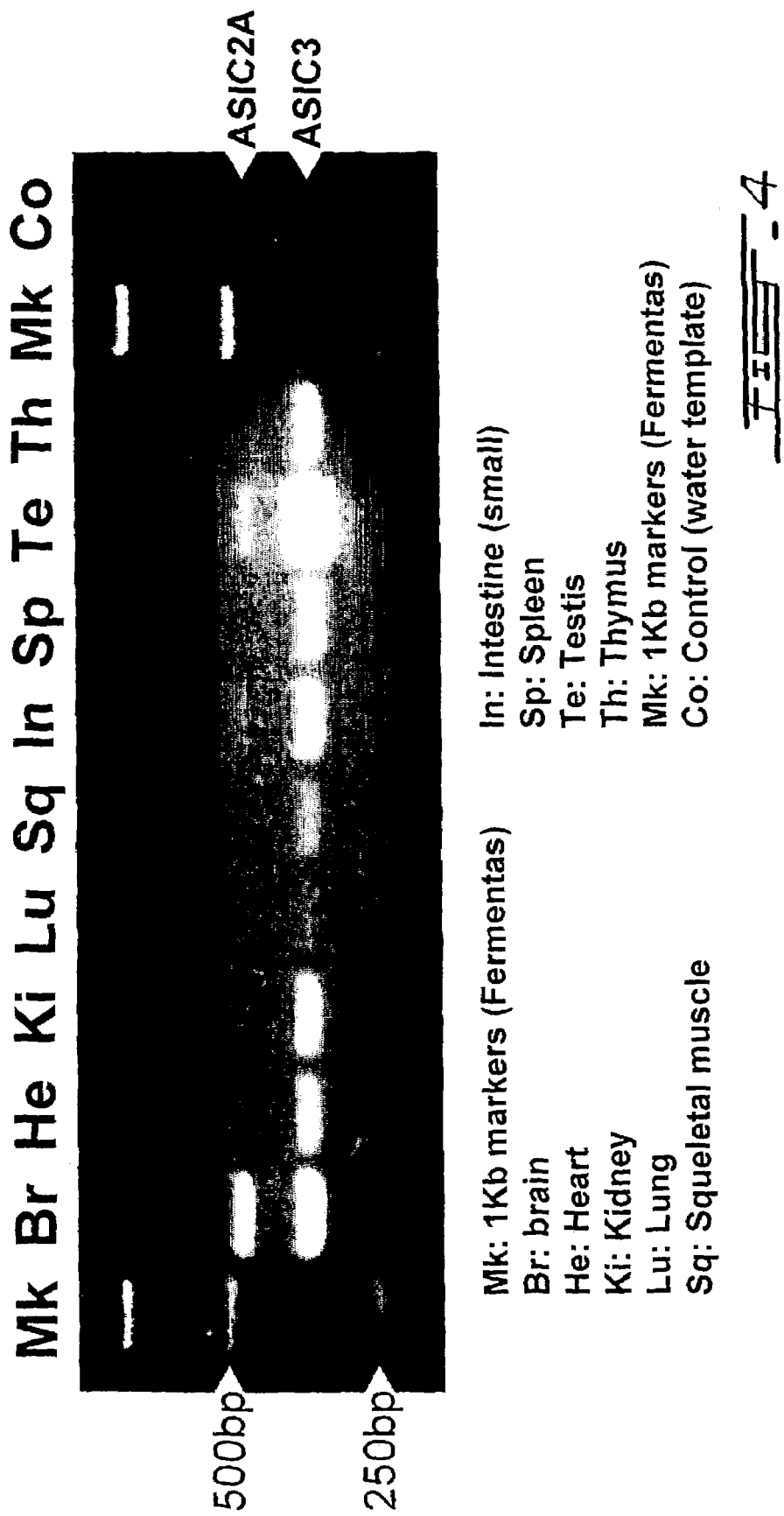
FIG. 4 represents an ethidium bromide stained agarose gel showing the expression pattern of mRNA for hASIC2A and hASIC3 determined by duplex RT-PCR amplification of commercially available human RT-cDNA (Clontech) using specific oligonucleotide primers for each subunit. Noteworthy is the co-expression of both subunits in trigeminal ganglia, suggesting that the heteromultimeric receptor, ASIC-2S.2 might be involved in pain and/or sensory transmission.

In another embodiment of the invention, ASIC-2S.2 heteromultimeric channels may be used for therapeutic purposes. Based on the mRNA distribution patterns of ASIC2A and ASIC3 showing that ASIC2A and ASIC3 transcripts are primarily but not exclusively associated with cells of the peripheral and central nervous systems, ASIC-2S.2 is believed to play a role in the regulation of neurotransmitter release, neuronal excitability, or excitotoxicity. Indeed, secretory granules and synaptic vesicles are known to contain high concentrations of protons (low intravesicular pH), which are co-released with other neurotransmitters during regulated and constitutive exocytosis. Released protons might thus activate pre- and/or post-synaptic, or extrasynaptic ASIC-2S.2 receptors. Indeed, under certain conditions, low pH or extracellular acidosis has been shown to influence synaptic transmission as well as the induction of long-term potentiation (Igelmund et al., Brain Res 1995; 689: 9; Velisek et al., Hippocampus 1998; 8: 24). Also, in certain animal seizure models, neuroprotective effects of low pH have been observed (Velisek et al., Exp Brain Res 1994; 101: 44). Thus, an important use of ASIC-2S.2 is screening for compounds that regulate neurotransmitter release, synaptic efficacy, neuroexcitability, or neurotoxicity. Such compounds may have utility in a number of physiological and pathological situations pertaining, for example, to cognition, perception, learning, memory, pain and many others. More specifically, in situ hybridization and duplex RT-PCR analysis (FIGS. 4 and 5) indicate that coexpression of ASIC2A and ASIC3 is region specific. Interestingly, in contrast to what is reported for the rat, we report herein for the first time that ASIC2A is highly expressed in human sensory ganglia, such as the trigeminal ganglia. Furthermore, the highest probability of coexpression of ASIC2A and ASIC3 has also been found in these sensory ganglia. This strongly suggests an important role for the ASIC-2S.2 channels in pain and/or somato-sensory transmission.

In one embodiment, antagonists or inhibitors of the ASIC-2S.2 protein complex or vectors expressing antisense sequences may be used to treat disorders and diseases of the nervous system resulting from altered ion transport, signal transmission, and apoptosis. Such diseases include, but are not limited to, chronic pain, neuropathic pain such as diabetic-, cancer-, and AIDS-related, neurodegenerative diseases such as Alzheimer's disease, Parkinson's disease, Huntington's disease, Creutzfeld-Jacob disease, and amyotrophic lateral sclerosis, and dementias, including AIDS-related, as well as convulsions, epilepsy, stroke, and anxiety and depression.

In another embodiment, antagonists or inhibitors of the ASIC-2S.2 protein complex or vectors expressing antisense sequences may be used to treat cardiovascular diseases such as angina, congestive heart failure, vasoconstriction, hypertension, atherosclerosis, restenosis, and bleeding.

Agonists, which enhance the activity and antagonists, which block or modulate the effect of ASIC-2S.2 may be used in those situations where such enhancement or inhibition is therapeutically desirable. Such agonists, antagonists or inhibitors may be produced using methods, which are generally known in the art, such as screening libraries of pharmaceutical agents for compounds, which directly (or indirectly) and specifically interact and/or bind ASIC-2S.2. Other methods involve the use of purified ASIC2A and/or ASIC3 to produce antibodies. For example, in one aspect, antibodies which are specific for ASIC2A or ASIC3, or ASIC-2S.2 may be used directly as an antagonist of ASIC-2S.2, or indirectly as a targeting or delivery mechanism for bringing a pharmaceutical agent to cells or tissue, which express ASIC-2S.2.

The antibodies may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with ASIC2A, or ASIC3, or with ASIC2A and ASIC3, including covalently linked ASIC2A-ASIC3 tandems and ASIC2A-ASIC3 chimers, or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the peptides, fragments, or oligopeptides used to induce antibodies to ASIC-2S.2 have an amino acid sequence consisting of at least five amino acids, and more preferably at least 10 amino acids. It is also preferable that they are identical to a portion of the amino acid sequence of the natural protein, and they may contain the entire amino acid sequence of a small, naturally occurring molecule. Short stretches of ASIC2A or ASIC3 amino acids may be fused with those of another protein such as keyhole limpet hemocyanin and antibody produced against the chimeric molecule.

Monoclonal antibodies to ASIC-2S.2 may be prepared using any technique which provides for the production of antibody molecules by continuous cell lines in culture. These include, but are not limited to, the hybridoma technique, the human B-cell hybridoma technique, and the EBV-hybridoma technique (Koehler et al. Nature 1975; 256: 495; Kosbor et al., Immunol Today 1983; 4: 72; Cote et al., Proc Natl Acad Sci 1983; 80: 2026; Cole et al., "Monoclonal Antibodies and Cancer Therapy", Alan R. Liss Inc., 1985, New York, N.Y., pp. 77-96).

In addition, techniques developed for the production of "chimeric antibodies", the splicing of mouse antibody genes to human antibody genes to obtain a molecule with appropriate antigen specificity and biological activity can be used (Morrison et al. (1984) Proc. Natl. Acad. Sci. 81:6851-6855; Neuberger et al. (1984) Nature 312:604-608; Takeda et al. (1985) Nature 314:452-454). Alternatively, techniques described for the production of single chain antibodies may be adapted, using methods known in the art, to produce ASIC-2S.2-specific single chain antibodies. Antibodies with related specificity, but of distinct idiotypic composition, may be generated by chain shuffling from random combinatorial immunoglobin libraries (Burton, D. R. (1991) Proc. Natl. Acad. Sci. 88:11120-3).

Antibodies may also be produced by inducing in vivo production in the lymphocyte population or by screening recombinant immunoglobulin libraries or panels of highly specific binding reagents as disclosed in the literature (Orlandi et al. (1989) Proc. Natl. Acad. Sci. 86: 3833-3837; Winter, G. et al. (1991) Nature 349:293-299).

Antibody fragments which contain specific binding sites for ASIC-2S.2 may also be generated. For example, such fragments include, but are not limited to, the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed to allow rapid and easy identification of monoclonal Fab fragments with the desired specificity (Huse et al. (1989) Science 256:1275-1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between ASIC-2S.2 and its specific antibody. A two-site, monoclonal-based immunoassay utilizing monoclonal antibodies reactive to two non-interfering ASIC-2S.2 epitopes is preferred, but a competitive binding assay may also be employed (Maddox, supra).

In another embodiment of the invention, the polynucleotides encoding ASIC2A and/or ASIC3, or any fragment thereof, or antisense sequences, may be used for therapeutic purposes. In one aspect, antisense to the polynucleotide encoding ASIC2A and/or ASIC3 may be used in situations in which it would be desirable to block the synthesis of the ASIC-2S.2 protein complex. In particular, cells may be transformed with sequences complementary to polynucleotides encoding ASIC2A and/or ASIC3. Thus, antisense sequences may be used to modulate ASIC-2S.2 activity, or to achieve regulation of gene function. Such technology is now well known in the art, and sense or antisense oligomers or larger fragments, can be designed from various locations along the coding or control regions of sequences encoding ASIC2A and/or ASIC3.

Expression vectors derived from retroviruses, adenovirus, herpes or vaccinia viruses, or from various bacterial plasmids may be used for delivery of nucleotide sequences to the targeted organ, tissue or cell population. Methods, which are well known to those skilled in the art, can be used to construct recombinant vectors which will express antisense polynucleotides of the genes encoding ASIC2A and/or ASIC3. These techniques are described both in Sambrook et al. (supra) and in Ausubel et al. (supra).

Genes encoding ASIC2A and/or ASIC3 can be turned off by transforming a cell or tissue with expression vectors which express high levels of a polynucleotide or fragment thereof which encodes ASIC2A and/or ASIC3. Such constructs may be used to introduce untranslatable sense or antisense sequences into a cell. Even in the absence of integration into the DNA, such vectors may continue to transcribe RNA molecules until all copies are disabled by endogenous nucleases. Transient expression may last for a month or more with a non-replicating vector and even longer if appropriate replication elements are part of the vector system.

As mentioned above, modifications of gene expression can be obtained by designing antisense molecules, DNA, RNA or PNA, to the control regions of the gene encoding ASIC2A or ASIC3, i.e., the promoters, enhancers, and introns. Oligonucleotides derived from the transcription initiation site, e.g., between positions −10 and +10 from the 5' end of the transcript, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and Carr, B. I. Molecular and Immunologic Approaches, Futura Publishing Co., Mt. Kisco, N.Y.). The antisense molecules may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding ASIC2A and/or ASIC3.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro and in vivo transcription of DNA sequences encoding ASIC2A and/or ASIC3. Such DNA sequences may be incorporated into a wide variety of vectors with suitable RNA polymerase promoters such as T7 or SP6. Alternatively, these cDNA constructs that synthesize antisense RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection and by liposome injections may be achieved using methods which are well known in the art.

Any of the therapeutic methods described above may be applied to any suitable subject including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of ASIC-2S.2, or any component thereof, antibodies to ASIC-2S.2, mimetics, agonists, antagonists, or inhibitors of ASIC-2S.2. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hank's solution, Ringer's solution, or physiologically buffered saline. Aqueous injection suspensions may contain substances, which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1-50 mM histidine, 0.1%-2% sucrose, and 2-7% mannitol, at a pH range of 4.5 to 5.5, that is combined with buffer prior to use.

After pharmaceutical compositions have been prepared, they can be placed in an appropriate container and labeled for treatment of an indicated condition. For administration of ASIC-2S.2, or any component thereof, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rats, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example ASIC-2S.2 or any component or fragment thereof, antibodies against ASIC-2S.2, agonists, antagonists or inhibitors of ASIC-2S.2, which ameliorates the symptoms or condition. Therapeutic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $LD_{50}/ED_{50}$.

Pharmaceutical compositions, which exhibit large therapeutic indices are preferred. The data obtained from cell culture assays and animal studies is used in formulating a range of dosage for human use. The dosage contained in such compositions is preferably within a range of circulating concentrations that include the $ED_{50}$ with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind ASIC-2S.2 may be used for the diagnosis of conditions or diseases characterized by expression of ASIC-2S.2, or in assays to monitor patients being treated with ASIC-2S.2 agonists, antagonists or inhibitors. The antibodies useful for diagnostic purposes may be prepared in the same manner as those described above for therapeutics. Diagnostic assays for ASIC-2S.2 include methods which utilize the antibody and a label to detect ASIC-2S.2, or any component therof, in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring ASIC-2S.2 are known in the art and provide a basis for diagnosing altered or abnormal levels of ASIC-2S.2 expression. Normal or standard values for ASIC-2S.2 expression are established by combining body fluids or cell extracts taken from normal mammalian subjects, preferably human, with antibody to ASIC-2S.2 under conditions suitable for complex formation. The amount of standard complex formation may be quantified by various methods, but preferably by photometric, means. Quantities of ASIC-2S.2 expressed in subject, control and disease, samples from biopsied tissues are compared with the standard values. Deviation between standard and subject values establishes the parameters for diagnosing disease.

In another embodiment of the invention, the polynucleotides encoding ASIC-2S.2 may be used for diagnostic purposes. The polynucleotides which may be used include oligonucleotide sequences, antisense RNA and DNA molecules, and PNAs. The polynucleotides may be used to detect and quantitate gene expression in biopsied tissues in which expression of ASIC-2S.2 may be correlated with disease. The diagnostic assay may be used to distinguish between absence, presence, and excess expression of ASIC-2S.2, and to monitor regulation of ASIC-2S.2 levels during therapeutic intervention. The diagnostic assay may also be used to determine the ratio of expression between ASIC2A and ASIC3, and any changes in these expression rations, as an index or marker of ASIC-2S.2 expression.

In one aspect, hybridization with PCR probes which are capable of detecting polynucleotide sequences, including genomic sequences encoding ASIC2A or ASIC3 or closely related molecules, may be used to identify nucleic acid sequences which encode ASIC2A or ASIC3. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding ASIC2A or ASIC3, alleles, or related sequences.

Probes may also be used for the detection of related sequences, and should preferably contain at least 50% of the nucleotides from any of the ASIC2A or ASIC3 encoding sequences. The hybridization probes of the subject invention may be DNA or RNA and derived from the nucleotide sequence of SEQ ID NO: 1, SEQ ID NO: 3, SEQ ID NO: 5 or SEQ ID NO:7, or from genomic sequences including promoter, enhancer elements, and introns of the naturally occurring ASIC2A and ASIC3.

Means for producing specific hybridization probes for DNAs encoding ASIC2A or ASIC3 include the cloning of nucleic acid sequences encoding ASIC2A or ASIC3 derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as $^{32}P$ or $^{35}S$, or enzymatic labels, such as alkaline phosphatase coupled to the probe via avidin/biotin coupling systems, and the like.

Polynucleotide sequences encoding ASIC2A and/or ASIC3 may be used for the diagnosis of conditions or diseases which are associated with expression of ASIC-2S.2. Examples of such conditions or diseases include neurological diseases including chronic pain, neuropathic pain such as diabetic-, cancer-, and AIDS-related neurodegenerative diseases such as Alzheimer's disease, Parkinson's disease, Huntington's disease, Creutzfeld-Jacob disease, and amyotrophic lateral sclerosis, and dementias, such as AIDS-related, as well as convulsions, epilepsy, stroke, and anxiety and depression, cardiovascular diseases such as angina, congestive heart failure, vasoconstriction, hypertension, atherosclerosis, restenosis, and bleeding. The polynucleotide sequences encoding ASIC2A or ASIC3 may be used in Southern or northern analysis, dot blot, or other membrane-based technologies; in PCR technologies; or in dip stick, pin, ELISA or chip assays utilizing fluids or tissues from patient biopsies to detect altered ASIC-2S.2 expression. Such qualitative or quantitative methods are well known in the art.

In a particular aspect, the nucleotide sequences encoding ASIC2A and/or ASIC3 may be useful in assays as probes that detect activation or induction of various neurological or other non-neurological disorders, particularly those mentioned above. The nucleotide sequence encoding ASIC2A and/or ASIC3 may be labelled by standard methods and added to a fluid or tissue sample from a patient under conditions suitable for the formation of hybridization complexes. After a suitable incubation period, the sample is washed and the signal is quantified and compared with a standard value. If the amount of signal in the biopsied or extracted sample is significantly different from that of a comparable control sample, this indicates that the levels of nucleotide sequences that hybridized with the labelled probe in the sample are also different. The presence of altered levels of nucleotide sequences encoding ASIC2A and/or ASIC3 in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of ASIC-2S.2, a normal or standard profile for expression is established. This may be accomplished by combining body fluids or cell extracts taken from normal subjects, either animal or human, with a sequence, or a fragment thereof, which encodes ASIC2A and/or ASIC3 under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to neurological diseases, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventive measures or aggressive treatment earlier thereby preventing the development or further progression of the disease.

Additional diagnostic uses for oligonucleotides encoding ASIC2A and/or ASIC3 may involve the use of PCR. Such oligomers may be chemically synthesized, generated enzymatically, or produced from a recombinant source. Oligomers will preferably consist of two nucleotide sequences, one with sense orientation and another with antisense, employed under optimised conditions for identification of a specific gene or condition. The same two oligomers, nested sets of oligomers, or even a degenerate pool of oligomers may be employed under less stringent conditions for detection and/or quantification of closely related DNA or RNA sequences.

Methods which may also be used to quantify the expression of ASIC-2S.2 include radiolabelling or biotinylating nucleotides, coamplification of a control nucleic acid, and standard curves onto which the experimental results are interpolated (Melby P C et al. J Immunol Methods, 1993; 159: 235; Duplaa C et al. Anal Biochem 1993; 229). The speed of quantification of multiple samples may be accelerated by running the assay in an ELISA format where the oligomer of interest is presented in various dilutions and a spectrophotometric or calorimetric response gives rapid quantification.

Screening Assays

In another embodiment of the invention, ASIC-2S.2, its active, catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between ASIC-2S.2 and the agent being tested, may be measured. Thus, the polypeptides derived from ASIC-2S.2, or any component thereof, may also be used to assess the binding of small molecule substrates and ligands in, for example, cells, cell-free preparations, chemical libraries, and natural product mixtures. These substrates and ligands may be natural substrates and ligands or may be structural or functional mimetics. In general, such screening procedures involve producing appropriate cells, which express the receptor polypeptide complex of the present invention on the surface thereof. Such cells include cells from mammals, yeast, insects (e.g. *Drosophila*) or bacteria (e.g. *E. coli*). Cells expressing the receptor (or cell membranes containing the expressed receptor) are then contacted with a test compound to observe binding, or stimulation or inhibition of a functional response (for example inhibition of proton-activated currents).

The assays may simply test binding of a candidate compound wherein adherence to the cells bearing the receptor is detected by means of a label directly or indirectly associated with the candidate compound or in an assay involving competition with a labelled competitor. Further, these assays may test whether the candidate compound results in a signal generated by activation of the receptor, using detection systems appropriate to the cells bearing the receptor at their surfaces (for example increased ion permeation measured by patch clamp or, preferably by ion imaging with ion-specific dyes). Inhibitors of activation are generally assayed in the presence of a known agonist (for example protons) and the effect of the candidate compound on the activation by the agonist is observed. Standard methods for conducting such screening assays are well understood in the art. Typically, the response may be measured by use of a microelectrode technique accompanied by such measurement strategies as voltage clamping of the cell whereby activation of ion channels may be identified by inward or outward current flow as detected using the microelectrodes. $^{22}$Na, $^{86}$Rb, $^{45}$Ca radiolabelled cations or $^{14}$C or $^{3}$H guanidine may be used to assess such ion flux; a sodium, calcium or potassium ion sensitive dye (such as Fura-2, or Indo) may also be used to monitor ion passage through the receptor ion channel, or a potential sensitive dye may be used to monitor potential changes, such as in depolarisation.

Alternatively, it is also possible to mutate the ASIC2A and/or ASIC3 cDNA in order to produce a constitutively active ASIC-2S.2 channel, as has been shown with other DEG/ENaC family members (Huang et al., Nature 367: 467; Waldman et al., J Biol Chem 1997: 271; 10433, Sakai et al., J Physiol 1999; 519: 323, Schaefer et al., FEBS Lett 2000; In Press). Then, the constitutively active channel may be expressed in host cells to produce a screening assay where channel activity is permanent. The recording of channel activity my be carried out either by membrane voltage analysis, directly (patch clamp, for example) or indirectly (fluorescent probes, for example) or by sodium entry measurement (radioactive sodium influx, fluorescent probes, or reporter genes).

Another technique for drug screening, which may be used, provides for high throughput screening of compounds having suitable binding affinity to the protein of interest as described in published PCT application WO84/03564. In this method, as applied to ASIC-2S.2, large numbers of different small test compounds are synthesised on a solid substrate, such as plastic pins or some other surface. The test compounds are reacted with ASIC-2S.2, or components, or fragments thereof, and washed. Bound ASIC-2S.2 is then detected by methods well known in the art. Purified ASIC-2S.2, or any component thereof, can also be coated directly onto plates for use in the aforementioned drug screening techniques. Alternatively, non-neutralising antibodies can be used to capture the peptide and immobilise it on a solid support.

In another embodiment, one may use competitive drug screening assays in which neutralising antibodies capable of binding ASIC-2S.2 specifically compete with a test compound for binding ASIC-2S.2. In this manner, the antibodies can be used to detect the presence of any peptide which shares one or more antigenic determinants with ASIC-2S.2.

In additional embodiments, the nucleotide sequences which encode the individual components of ASIC-2S.2, namely ASIC2A and ASIC3, may be used in any molecular biology or pharmacology techniques that have yet to be developed, provided the new techniques rely on properties of the nucleotide or polypeptide sequences that are currently known, including, but not limited to, such properties as the triplet genetic code and specific base pair interactions.

EXAMPLES

The following examples are intended to further illustrate the invention and are not intended to limit the scope of the invention in any way. All references cited herein, whether previously or in the following examples, are expressly incorporated in their entirety by reference. All oligonucleotides disclosed in the following examples are designed using two recognised software packages: GeneWorks 2.5.1 and MacVector 6.0.1 (Oxford Molecular).

Example 1

Vector Constructs for the Functional Expression of ASIC-2S.2 Channels

Method 1: Expression of ASIC-2S.2 is accomplished by introducing into appropriate host cells, by various injection or transfection techniques known to one skilled in the art, two separate vectors comprising the nucleic acids encoding, respectively, the ASIC2A and ASIC3 polypeptides of SEQ ID NO:2 or NO:6 and SEQ ID NO: 4 or NO:8. A preferred eukaryotic expression vector is pcDNA3 (InVitrogen), or any derivatives thereof. Based on nucleic acid sequences of SEQ ID NO:1, SEQ ID NO:3, SEQ ID NO:5 and SEQ ID NO:7, specific oligonucleotide primers are designed immediately upstream and downstream, respectively, of the initiation and the stop codons. All primers are extended to add artificial restriction sites (e.g. forward primers with EcoRI and reverse primers with XbaI), allowing RT-PCR amplified full length nucleic acids to be directionally subcloned into pcDNA3. Ligated products are used to transform *E. Coli* strain DH5α from which purified plasmids are prepared using commercially available kits (Quiagen).

Method 2: Expression of ASIC-2S.2 is achieved by introducing into appropriate host cells, by various injection or transfection techniques known to one skilled in the art, a biscistronic vector comprising two nucleic acids encoding, respectively, ASIC2A and ASIC3 polypeptides of SEQ ID NO:2 or NO:6 and SEQ ID NO: 4 or NO:8. Bicistronic expression vectors produce one transcript with two translation initiation points, resulting in the simultaneous expression of two genes of interest. A preferred bicistronic vector is pIRES (Clontech) which permits the subcloning of two distinct genes in two separate multiple cloning sites (MCS A and B) located on either side of the internal ribosome entry site (IRES) from the encephalomyocarditis virus (ECMV). This allows the translation of two consecutive open reading frames from the same messenger RNA (Jang S K et al. J. Virol. 1990; 62: 2636—Rees S et al.: BioTechniques 1996; 20: 102). The MCSs and IRES sequences are downstream of the immediate early promoter of cytomegalovirus (PCMV IE). The intervening sequence (IVS) between PCMV IE and the MCS is an intron that is efficiently spliced out following transcription. SV40 polyadenylation signals downstream of the MCS direct proper processing of the 3' end of the mRNA from subcloned genes. Bacteriophage T7 and T3 promoters are located upstream and downstream of MCS A and B, respectively. pIRES uses the neomycin resistance gene (Neor) to permit selection of transformed cells. Neor is expressed from the SV40 enhancer/promoter, and a synthetic polyadenylation signal directs proper processing of the 3' end of the Neor mRNA. The SV40 origin also allows for replication in mammalian cells expressing the SV40 T antigen. The vector backbone also contains the β-lactamase gene for ampicillin resistance and a ColE1 origin of replication for propagation in *E. coli* and a f1 origin for single-stranded DNA production. As described above in method 1, RT-PCR amplified ASIC2A and ASIC3 nucleic acids are directionally subcloned, respectively, into MCS A and MCS B (or vice versa). Control vectors comprising two copies of ASIC2A- or ASIC3-encoding nucleic acids are also constructed. Ligated products are used to transform *E. Coli* strain DH5α from which purified plasmids are prepared using commercially available kits (Quiagen).

Method 3: Expression of ASIC-2S.2 is achieved by introducing into appropriate host cells, by various injection or transfection techniques known to one skilled in the art, an expression vector comprising an engineered chimeric nucleic acid which encodes both ASIC2A and ASIC3 polypeptides as a single tandem polypeptide delimited by the initiation methionine of the first subunit and the stop of the second subunit. The following example illustrates this method: The full length coding sequence of human ASIC3 is subcloned into pCDN3 between HindIII and EcoRI sites (plasmid A), while ASIC2A coding nucleic acid sequence is subcloned between EcoRI and XbaI (plasmid B). An ASIC3-specific forward primer just upstream of a natural NcoI site (SEQ ID NO:9) is paired with a mutagenic oligonucleotide primer designed to eliminate the stop codon and add an artificial EcoRI site (SEQ ID NO:10). A 570 bp fragment is amplified by PCR using the proof-reading DNA polymerase pfu (Stratagene). Following digestion with NcoI and EcoRI, the purified fragment is then back-cloned into the ASIC3-containing plasmid A in replacement of the corresponding wild type fragment. In the second step, the above mutated ASIC3 full length nucleic acid is cut out from the vector with HindIII and EcoRI and subcloned immediately upstream and in frame of the ASIC2A coding sequence of plasmid B. A number of different strategies can be designed to prepare similar constructs and the previous example is intended solely to illustrate this method and not to limit its scope in any way. The method also encompasses constructs where ASIC2A is placed upstream of ASIC3 as well as constructs where more than two subunits are attached together in any pertinent combination and synthesised as a single polypeptide.

Example 2

Expression of Functional ASIC-2S.2 Channels in *Xenopus laevis* Oocytes

According to method 1 described above, nuclei of *Xenopus* oocytes are injected with ASIC2A and ASIC3 cDNAs separately subcloned into pcDNA3 expression vector (1-5 ng). Control oocytes are injected with $H_2O$. Oocytes are maintained at 18° C. in modified Barth's solution. Proton-activated currents are measured by two-electrode voltage clamp 1-3 days after injection. During voltage clamp (−60 mV/−100 mV)), oocytes are bathed in 116 mM NaCl, 2 mM KCl, 1.8 mM $CaCl_2$, 10 mM acetic acid and 5 mM Hepes (pH 7.4 with NaOH). To determine proton-gating, bath solution is quickly switched to a solution of pH<7.4 for 10 sec, then returned to bath solution for washout. The stimulating solution is prepared by lowering the pH of the original bath solution with hydrochloric acid. The osmolality of the solutions is verified with an osmometer and corrected with mannitol or choline chloride. To document ionic selectivity, NaCl is replaced with LiCl or KCl. Current-voltage relationships are determined by stepping from a holding potential of −60 mV to potentials between −100 and +60 mV for 10 seconds before and during stimulation with low pH solution. FIGS. 1A (human) and 1B (rat) compare proton-activated currents carried by homomultimeric ASIC2A and ASIC3 receptors to the heteromultimeric ASIC-2S.2 receptors (ASIC2a+3). The much greater amplitude and the consistent biphasic profile of the current recorded in co-injected oocytes clearly reveals the existence of a novel proton-gated channel resulting from the assembly of ASIC2A and ASIC3. Species differences are also noteworthy. Indeed, using human subunits, both the early fast and sustained currents are strongly potentiated, while in the case of rat, the major effect appears to be on the sustained current only.

Figure 2:
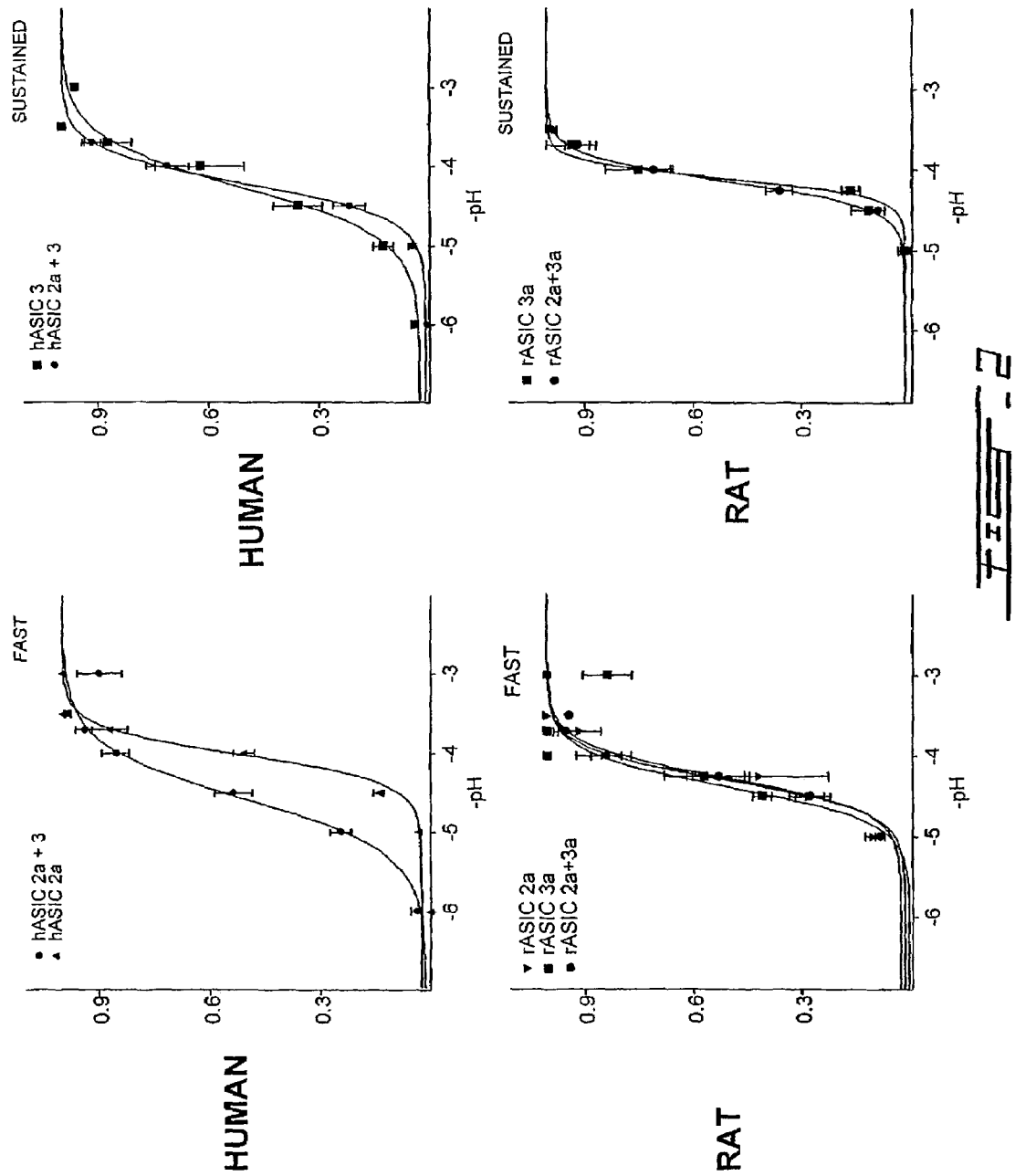
FIG. 2 shows the pH dose-response curves of proton-induced inward currents in human and rat homomultimeric (ASIC2A or ASIC3) and heteromultimeric (ASIC-2S.2)-expressing oocytes.

FIG. 2 compares pH-response curves of homomultimeric and heteromultimeric ASIC channels of the present invention.

The oocyte expression system is also used to test and screen for compounds with agonist or antagonist activity. FIGS. 5A and 5B illustrate this principal by showing the inhibitory effects of amiloride and gadolinium on proton-activated currents.

Example 3

Tissue Distribution of ASIC2A and ASIC3 Transcripts Using RT-PCR

To document the co-expression of ASIC2A and ASIC3 mRNA in various tissues, specific oligonucleotide primers are designed and used in a duplex RT-PCR protocol. Fragments of 470 and 340 bp are amplified, respectively, with ASIC2A-specific (SEQ ID NO: 11 and SEQ ID NO: 12) and ASIC3-specific (SEQ ID NO:13 and SEQ ID NO:14) primers, enabling the co-amplification of both fragments from a single sample. The reaction is carried out with the EXPAND long-template polymerase mix, containing both Taq and Pwo polymerases (Roche), according to the manufacturer's instructions. Briefly, the reaction mix includes: dNTPs 0.5 mM, forward and reverse primers 1 µM each, RT-cDNA template 5 µL, 10×PCR buffer 5 µL and polymerase enzyme mix 0.75 µL, all in a final volume of 50 µL. Samples are kept at 4° C. and the enzyme mix is added last. Tubes are then immediately transferred to the thermocycler preheated to 94° C., after which cycling is launched. Typical cycling conditions are as follows: Initial denaturation step: 2 min at 94° C., than 40 cycles of 45 sec at 94° C., 45 sec at 58° C. and 2 min at 72° C., followed by a final extension step of 10 min at 72° C. RT-cDNAs are either commercial (Clontech) or prepared from RNA or mRNA either with Superscript or Thermoscript enzyme mixes, according to the manufacturer's directions (Gibco Life Sciences). RNA and mRNA are prepared using standard molecular biology protocols, such as decribed in Maniatis et al., (see above) or using commercially available kits, such as the S.N.A.P. total RNA isolation kit, Fast Track 2.0 and micro Fast Track 2.0 mRNA isolation kits (InVitrogen). An example of tissue distribution of hASIC2A and hASIC3 mRNA expression appears in FIG. 4. Trigeminal ganglia are among tissues with the highest coexpression, suggesting that the heteromultimeric ASIC-2S.2 channel might be involved in pain and/or sensory transmission. This constrasts with previous results reported for rat where ASIC2A is apparently not expressed in sensory neurons.

Example 4

Co-localisation of ASIC2A and ASIC3 Transcripts Demonstrated by In Situ Hybridization Hybridization probes derived from SEQ ID NO:1, SEQ ID NO:3, SEQ ID NO:5 and/or SEQ ID NO:7 are employed to screen cDNAs, genomic DNAs, or mRNAs. An example of such use is in situ hybridization to mRNAs. Briefly, a 278 bp fragment corresponding to nucleotides 181-459 of rat ASIC2A ($Ser^{61}$-$Met^{153}$) is subcloned between Sac I and Sph I sites of the pGEM5zf vector. A 378 bp fragment of rat ASIC3, corresponding to nucleotides 1142-1520 of ASIC3 ($Leu^{381}$-$Pro^{507}$), is subcloned between Sac I and Apa I sites of the pGEM5zf vector. Sense and antisense cRNAs are synthesized with the SP6 and T7 RNA polymerases in the presence of [$^{32}P$]-UTP for Northern blot or a mix of [$^{35}S$]-CTP and [$^{35}S$]-UTP for in situ hybridization. For the latter, 6 ηm-thick tissue sections are fixed for 1 hr with 4% formaldehyde in 0.1 M phosphate buffer (pH 7.2) and washed extensively with phosphate buffered saline (PBS), then reacted with acetic anhydride in triethanolamine 0.1 M solution. Then, the sections are hybridized overnight at 55° C. using the double [$^{35}S$]-CTP and [$^{35}S$]-UTP-labelled cRNA probes. After extensive washing, the sections are dried and exposed to X-ray film for 2-3 days (Marcinkiewicz et al. Neuroscience 1997; 76: 425). FIG. 5 shows an example in rat cerebellum where ASIC2A and ASIC3 positive grains are clearly present on the same cell type, namely the Golgi cells (GC) of the granular cell layer.

Example 5

Co-purification of ASIC2A and ASIC3 Subunits

The existence of a novel heteromultimeric proton-gated ion channel, initially revealed by electrophysiological data, is further corroborated by biochemical data providing direct evidence of the association between ASIC2A and ASIC3 subunits through protein/protein interactions. For this purpose, N- or C-terminal epitope-tagged fusion proteins are constructed with ASIC2A and ASIC3. For the C-terminus, mutagenic oligonucleotide primers eliminate the stop codons of ASIC2A and ASIC3 and respectively add an artificial XhoI and SalI restriction site to the 3' end. Then, the PCR-amplified full-length ASIC2A and ASIC3 cDNAs are subcloned between the artificial EcoRI-XhoI sites into a pcDNA3 vector containing an in frame cassette with a FLAG or $His_6$ epitope followed by an artificial stop codon. N-terminal $His_6$ tagging of ASIC3 is achieved by directly subcloning a full-length EcoRI-NotI ASIC3 fragment into the pcDNA3.1/HisA vector (Invitrogen). Similarly, a PCR-amplified full-length ASIC2A cDNA flanked with EcoRI-XhoI sites is subcloned into the pcDNA3.1/HisB vector (InVitrogen) as well as in the pEGFP-C1 vector (Clontech), providing, respectively, a N-terminal $His_6$- and GFP-tagged ASC2A. All the above ASIC2A and ASIC3 derivatives were done with human subunits, but a similar approach can also be done for the rat subunits, or any other species, by anyone skilled in the art. All new tagged receptors are tested for function before performing co-purification experiments. The results from the functional tests are summarised in FIG. 6B. For co-purification, the following combinations are either co-injected into oocytes or co-transfected into HEK 293 cells for transient expression:
1) ASIC2A-N_$His_6$+ASIC3-C_FLAG
2) 2) ASIC2A-N_GFP+ASIC2A-N_$His_6$
3) ASIC2A-N_GFP+ASIC3-N_$His_6$.
(Where "N_" indicates N-terminal tagging and "C_" indicates C-terminal tagging).

After the required time for protein expression, oocytes or cells are collected, lysed and membranes solubilized in a Triton X-100-containing buffer (Tinker et al., Cell 1996; 87: 857—Lê et al., J Neuroscience 1998; 18: 7152). Unsolubilized material is removed by centrifugation and supernatants are incubated with a Ni-NTA-resin (Quiagen) (2 and 3) or an immunoaffinity resin coupled with antiFLAG M2 monoclonal antibodies. After several washes, bound proteins are either eluted with 500 mM imidazole (Ni-NTA) or directly with the SDS-PAGE loading buffer. Proteins separated by gel electrophoresis are transferred onto nitrocellulose membranes (Amersham) and immunoprobed with commercially available antibodies against GFP (Green Fluorescent Protein) or $His_6$ epitopes, followed by peroxidase-labelled secondary antibodies for chemiluminescence detection (ECL kit, Amersham). Results from these experiments appear in FIGS. 7A (HEK 293 cells) and 7B (oocytes) and provide for the first time ever the proof of direct protein-protein interactions between ASIC2A and ASIC3 polypeptides. Indeed, both subunits are always purified together, independently of which subunit is initially targeted by the purification step. We have therefore provided direct biochemical evidence for the existence of the novel heteromultimeric ASIC-2S.2 receptor.

Example 6

Figure 3A:
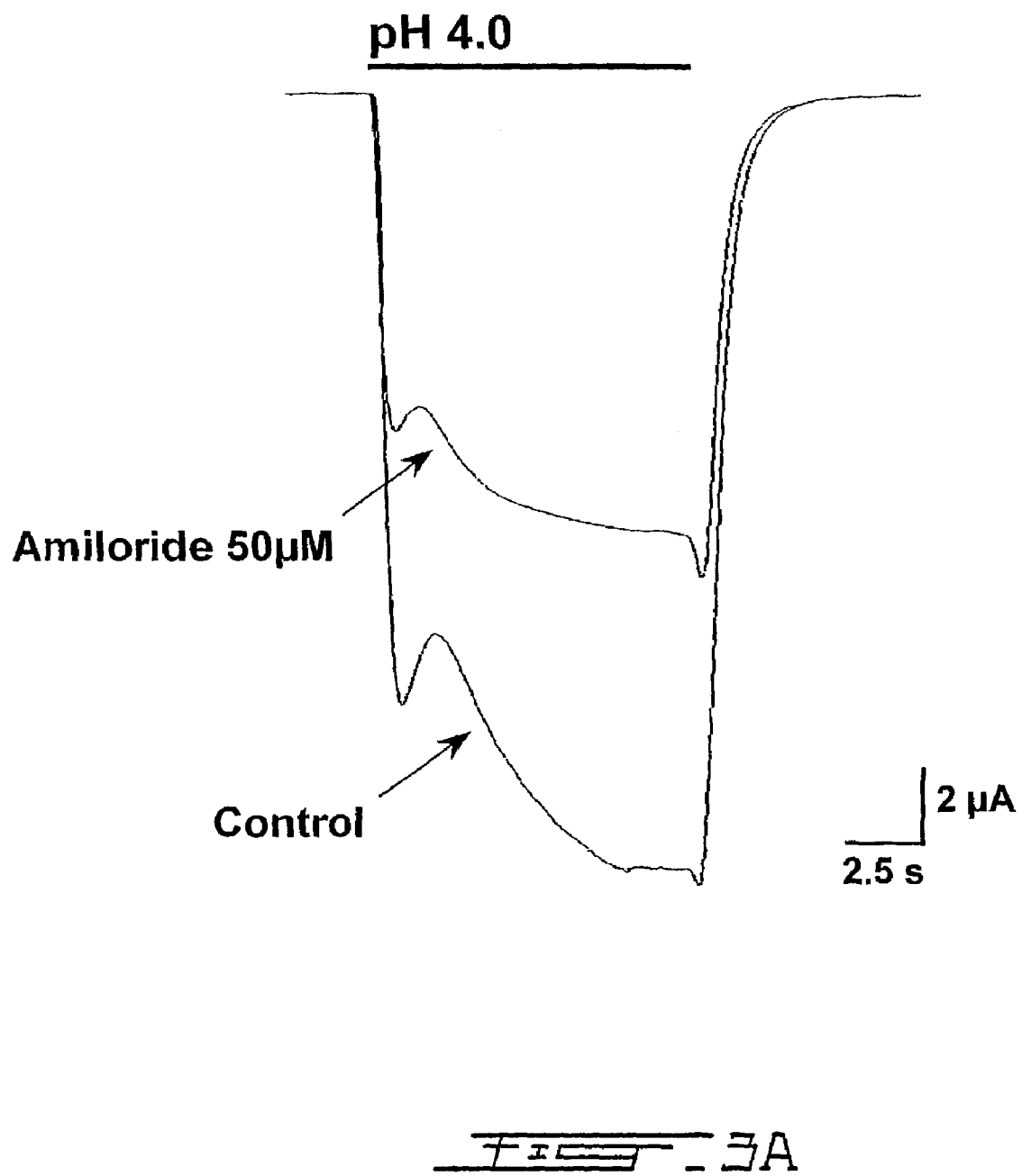
FIG. 3 shows the antagonistic effects of amiloride (A) and gadolinium ions (B) on proton-induced inward currents in human and rat homomultimeric (ASIC2A or ASIC3) and heteromultimeric (ASIC-2S.2)-expressing oocytes.

Screening for Compounds Capable of Modulating Ion Channel Activity and/or Properties As described in example 2, voltage clamped oocytes expressing the ASIC-2S.2 channels are used to screen for molecules capable of modulating, activating or inhibiting channel activity. See FIGS. 3A and 3B.

Alternatively, permanently or transiently transfected or infected cell lines (e.g. COS, HEK 293) expressing ASIC- 2S.2, cultured in multiwell plates, are loaded with potential- or cation-sensitive (sodium, calcium) dyes and the fluorescence emission is measured following application of control and low pH buffers (e.g. pH 7.4 and pH 5.0). The responses to both buffers in the presence and absence of candidate compounds are compared to identify compounds, which stimulate, inhibit or modulate ASIC-2S.2.

Figure 6A:
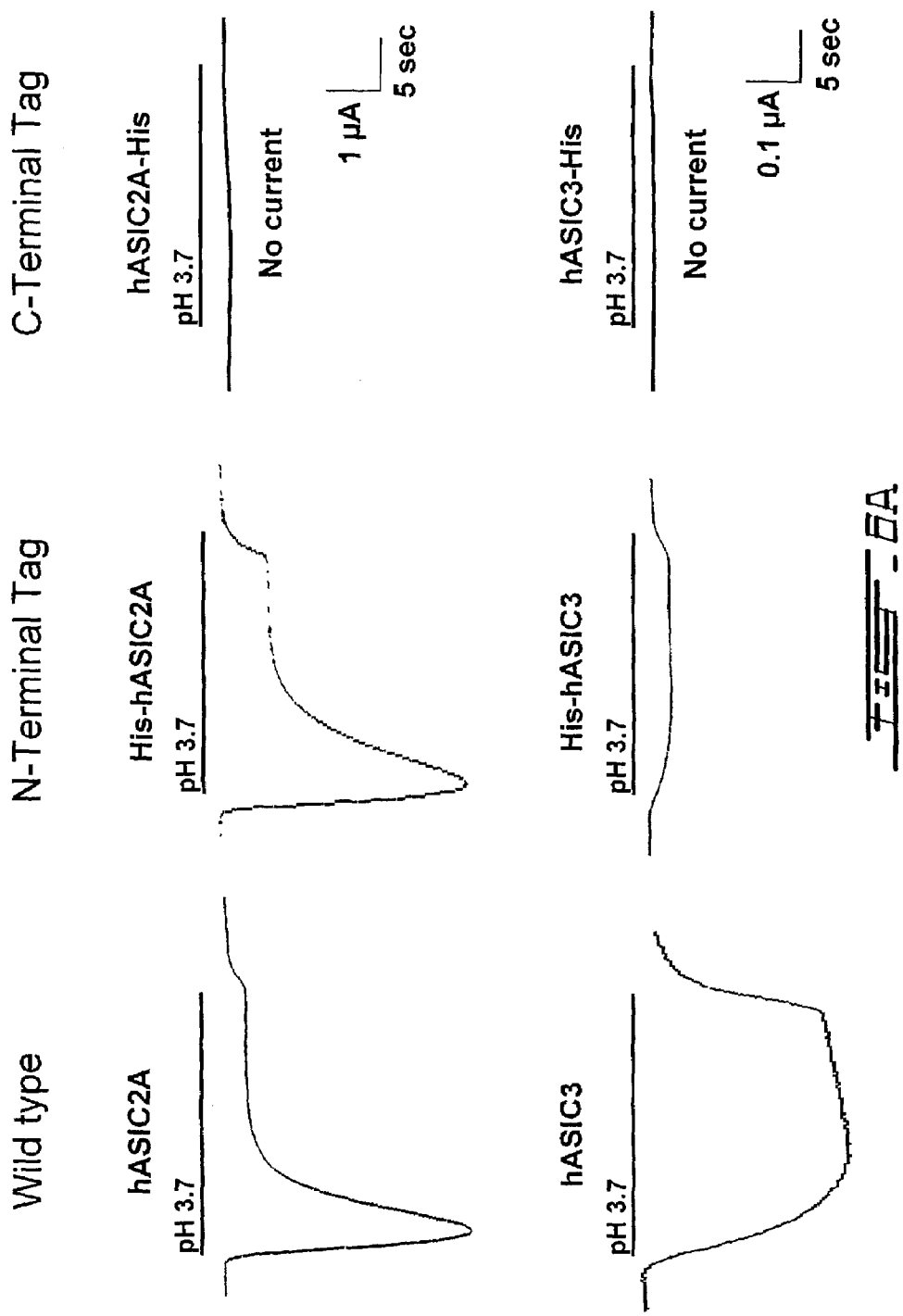
FIG. 6A gives examples of currents and FIG. 6B summarises results in a table format.
Figure 9A:
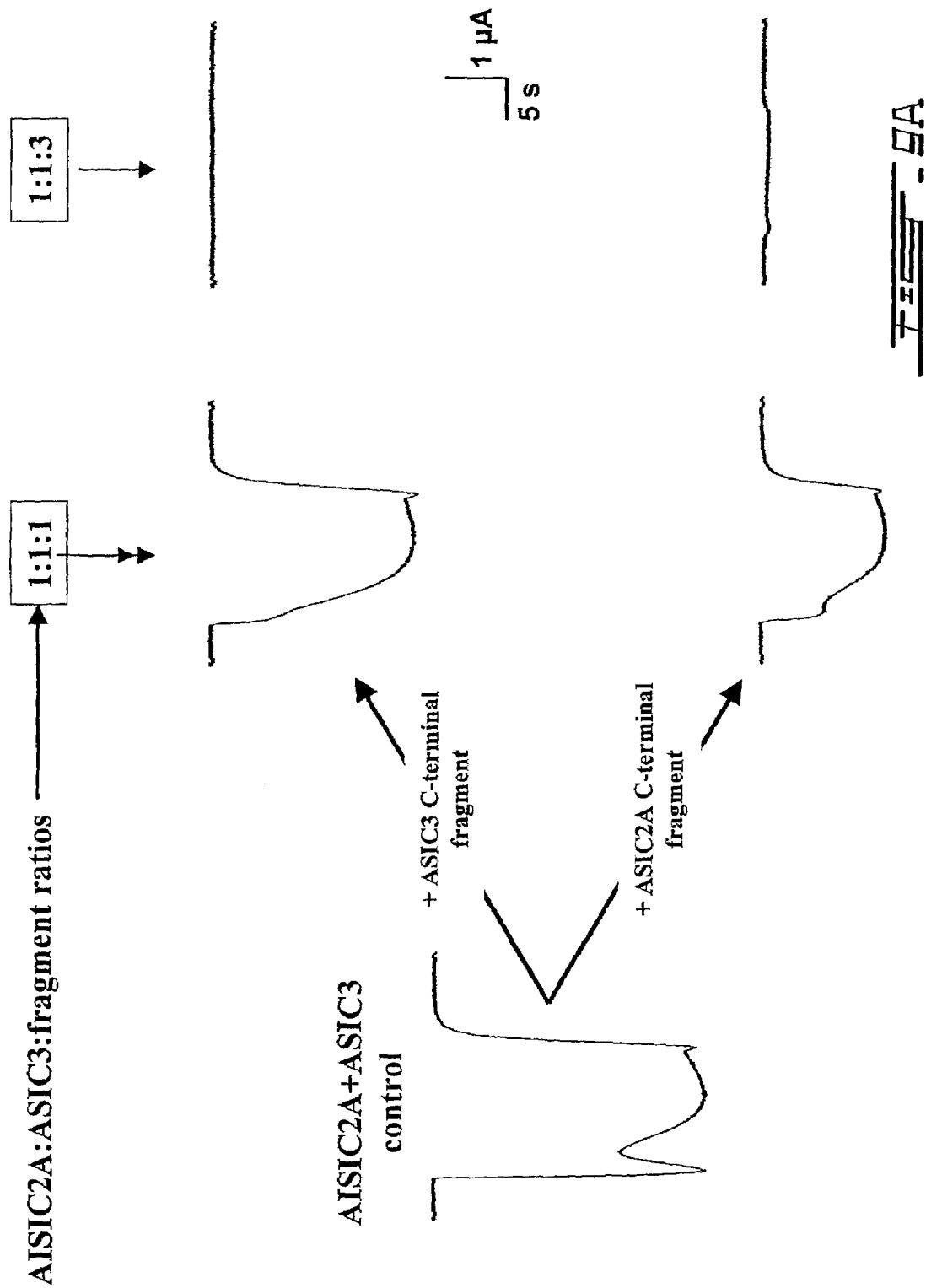
FIG. 9A shows the effects of the C-terminal fragments of ASIC3 (upper traces) and ASIC2A (lower traces).
Figures 12A, 12B:
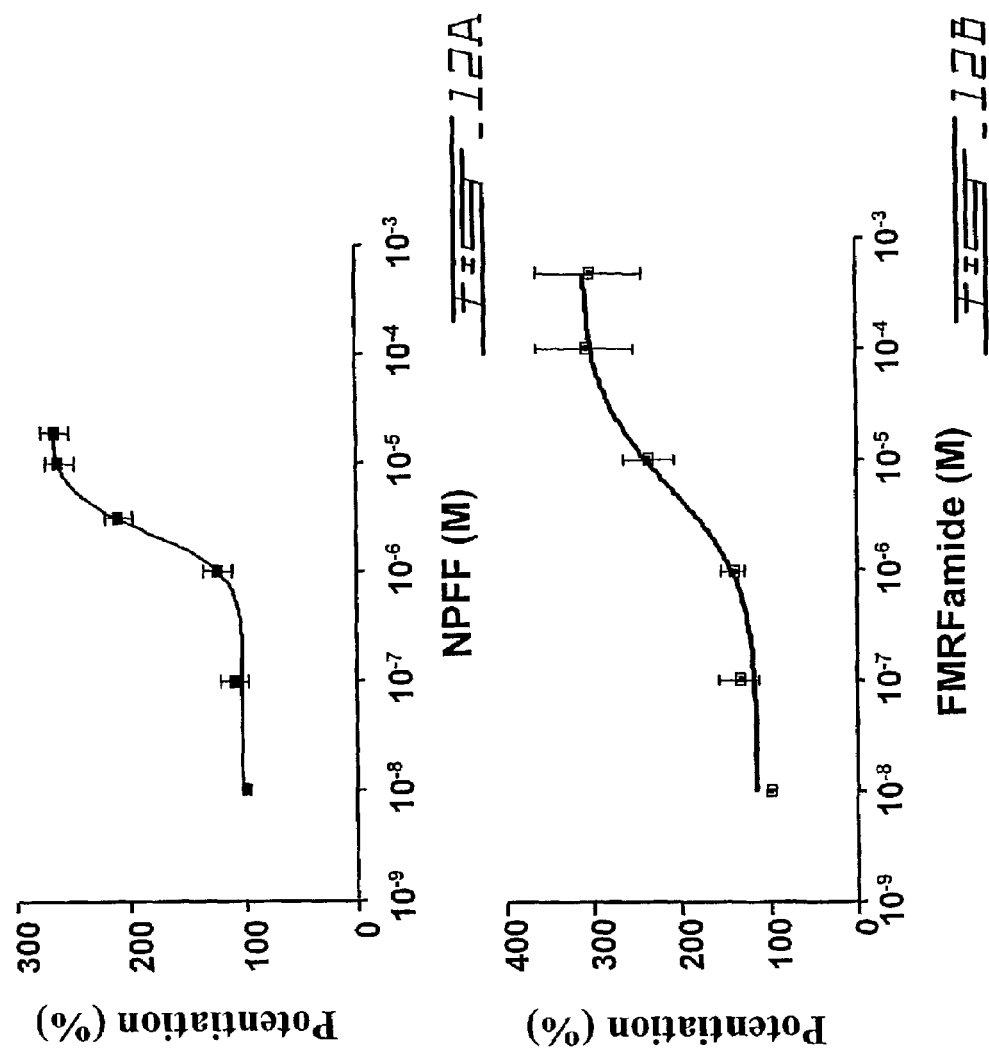
FIG. 12 Dose-response curves of NPFF (A) and FMRFamide (B) on the potentiation of currents induced by pH 4 on human ASIC2S.2 (ASIC2A+3) receptors. NPFF was found more potent ($EC_{50}=2$ µM, n=6) than FMRFamide ($EC_{50}=13$ µM, n=12) in modulating ASIC2S.2-mediated cation currents. Values are expressed as mean±SEM and represent % of response to pH 4 measured in presence of $10^{-8}$ M peptide.

Particular subclasses of channel antagonists are substances capable of disrupting protein-protein interactions between the subunits, which compose the ASIC-2S.2 channels. These compounds will either prevent the association of ASIC2A and ASIC3 into functional channels or dissociate already assembled ASIC-2S.2 receptors by binding to the specific protein domains responsible for ASIC subunit interactions. We have evidence indicating that the intracellular domains of ASIC2A and/or ASIC3 are involved in the assembly of functional channels. The C-termini appear to be particularly important since modifications to this domain generates non-functional subunits in both homo- and heteromultimeric form. Indeed, as seen in FIG. 6B, all N-terminally tagged ASIC2A or ASIC3 retain full function and ability to interact with a functional counterpart. In contrast, C-terminal tagging in most cases created non-functional, non-interacting subunits. Therefore, fusion proteins are constructed comprising only the intracellular domains of human ASIC2A or human ASIC3. Briefly, C-terminal fragments of ASIC3 and ASIC2A are amplified with mutagenic primers (SEQ ID NO:15 and NO:16 for hASIC3; SEQ ID NO:17 and NO:18, for hASIC2A) that add an in frame artificial initiation site at the 5' end, as well as artificial HindIII and BamHI restriction sites, used for subcloning of said fragments into pcDNA3 expression vectors. The resulting C-terminal nucleic acid and peptide fragments are indicated respectively in SEQ ID NO: 19 and SEQ ID NO: 20, for human ASIC3 and SEQ ID NO 21 and SEQ ID NO: 22 for human ASIC2A. Additionally, N-terminal fragments of ASIC3 and ASIC2A are constructed, by inserting an artificial stop codon with mutagenic primers (SEQ ID NO:23 and its reverse for hASIC3; SEQ ID NO:24 and its reverse for hASIC2A) using the commercially available mutagenesis kit QuickChange (Stratagene™), according to the manufacturer's directions. All fragments are inserted into the pcDNA expression vector. The resulting N-terminal nucleic acid and peptide fragments are indicated respectively in SEQ ID NO: 25 and SEQ ID NO: 26 for human ASIC3 and SEQ ID NO: 27 and SEQ ID NO: 28 for human ASIC2A. The inhibitory effects of these fragments on channel function and/or assembly is tested by co-expressing these truncated constructs together with wild-type ASIC2A and/or ASIC3 both in homomeric and heteromeric combinations (see FIGS. 9A and 9B). Additional fusion proteins with shorter fragments of the intracellular domains are used to identify the smallest amino acid sequence involved in the interaction of ASIC2A and ASIC3. This sequence of amino acids is validated by the inhibitory and/or disruptive effect of small peptides corresponding to the identified amino acid sequence, when said peptides are introduced into hosts expressing the ASIC-2S.2 heteromultimeric channel. A drug screening method based on the identified peptides is used to identify molecules capable of binding to them. Such compounds will, in turn, bind to the corresponding amino acid sequence present in the full-length wild-type subunits and inhibit therefore subunit assembly. A number of approaches can be used for this purpose. For example, candidate compounds previously arrayed and attached to multi-well plates are exposed to the above-described peptides, linked to an additional epitope. After washing steps, wells holding compounds that bind the specific amino acid sequence are revealed with an ELISA-type based assay using labelled antibodies against the grafted epitope Data obtained using different concentrations of the peptides are used to calculate values for the number, affinity, and association constants of the interaction.

A similar approach as described above is also used with the N-terminal fragments of ASIC2A and/or ASIC3. Briefly, mutagenic primers are designed to introduce an artificial stop codon just upstream of the sequence encoding the first putative transmembrane domain of ASIC2A or ASIC3. Using commercially available mutagenesis Kits (e.g. QuickChange, Stratagene), the above mutations are incorporated into the plamids comprising the ASIC2A or ASIC3 nucleic acids. When these mutated plasmids are introduced into relevant hosts, only the first portion corresponding to the N-terminal intracellular domain of the ASIC2A and/or ASIC3 polypeptides is translated. Coexpression of said fragments with full length ASIC2A and ASIC3 is done to document their effect on the assembly of ASIC-2S.2 channels. Drug screening methods based on the smallest active N-terminal fragment are performed as described above for the C-terminal fragments.

Example 7

Antisense Molecules

Antisense molecules to the sequences encoding the ASIC-2S.2 components, or any part thereof, are used to inhibit in vivo or in vitro expression of naturally occurring ASIC-2S.2. Although use of antisense oligonucleotides, comprising about 20 base-pairs, is specifically described, essentially the same procedure is used with larger cDNA fragments. An oligonucleotide based on the coding sequences of either ASIC2A or ASIC3 are used to inhibit expression of naturally occurring ASIC-2S.2. The complementary oligonucleotide is designed from the most unique 5' sequence of the coding region and used either to inhibit transcription by preventing binding to the upstream untranscribed sequence or translation of an ASIC2A- or ASIC3-encoding transcript by preventing ribosomes from binding. Using an appropriate portion of the 5' sequence of SEQ ID NO: 1, SEQ ID NO: 3, SEQ ID NO: 5 or SEQ ID NO: 7, an effective antisense oligonucleotide includes any 15-20 nucleotides spanning the region which translates into the 5' coding sequence of the polypeptides of SEQ ID NO: 2, SEQ ID NO: 4, SEQ ID NO: 6 or SEQ ID NO: 8.

All publications mentioned in the above specifications are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, electrophysiology or related fields are intended to be within the scope of the following claims.

What is claimed is:

1. A purified heteromultimeric acid-sensing ion channel comprising:
   (a) an ASIC2A polypeptide comprising an amino acid sequence at least 90% identical to the amino acid sequence set forth in SEQ ID NO:2 or SEQ ID NO:6, and
   (b) an ASIC3 polypeptide comprising an amino acid sequence at least 90% identical to the amino acid sequence set forth in SEQ ID NO:4 or SEQ ID NO:8, wherein the cation permeability of said channel is induced by an increase in proton ion concentration.

2. The purified heteromultimeric acid-sensing ion channel of claim 1, wherein the amino acid sequence of the ASIC2A polypeptide is at least 95% identical to the amino acid sequence set forth in SEQ ID NO:2 or SEQ ID NO:6.

3. The purified heteromultimeric acid-sensing ion channel of claim 1, wherein the amino acid sequence of the ASIC2A polypeptide is at least 97% identical to the amino acid sequence set forth in SEQ ID NO:2 or SEQ ID NO:6.

4. The purified heteromultimeric acid-sensing ion channel of claim 1, wherein the amino acid sequence of the ASIC3 polypeptide is at least 95% identical to the amino acid sequence set forth in SEQ ID NO:4 or SEQ ID NO:8.

5. The purified heteromultimeric acid-sensing ion channel of claim 1, wherein the amino acid sequence of the ASIC3 polypeptide is at least 97% identical to the amino acid sequence set forth in SEQ ID NO:4 or SEQ ID NO:8.

6. The purified heteromultimeric acid-sensing ion channel of claim 2, wherein the amino acid sequence of the ASIC3 polypeptide is at least 95% identical to the amino acid sequence set forth in SEQ ID NO:4 or SEQ ID NO:8.

7. The purified heteromultimeric acid-sensing ion channel of claim 2, wherein the amino acid sequence of the ASIC3 polypeptide is at least 97% identical to the amino acid sequence set forth in SEQ ID NO:4 or SEQ ID NO:8.

8. The heteromultimeric acid-sensing ion channel of claim 1, wherein the ASIC2A polypeptide comprises the amino acid sequence SEQ ID NO:2 or SEQ ID NO:6 and the ASIC3 polypeptide comprises the amino acid sequence SEQ ID NO:4 or SEQ ID NO:8.

9. A process for producing a heteromultimeric acid-sensing ion channel comprising, culturing a host cell that expresses a recombinant ASIC2A polypeptide comprising an amino acid sequence at least 90% identical to the amino acid sequence set forth in SEQ ID NO:2 or SEQ ID NO:6, and a recombinant ASIC3 polypeptide comprising an amino acid sequence at least 90% identical to the amino acid sequence set forth in SEQ ID NO:4 or SEQ ID NO:8, under conditions sufficient to express the recombinant ASIC2A and ASIC3 polypeptides.

10. A method of identifying an agonist of the heteromultimeric acid-sensing ion channel of claim 1, comprising:
  (a) contacting a cell expressing the heteromultimeric acid-sensing ion channel of claim 1 with a candidate compound; and
  (b) determining the ion permeability of the heteromultimeric acid-sensing ion channel in the presence and absence of the candidate compound,
wherein an increase in the ion permeability in the presence of the candidate compound indicates that the candidate compound is an agonist of the heteromultimeric acid-sensing ion channel.

11. A method of identifying an antagonist of the heteromultimeric acid-sensing ion channel of claim 1, comprising:
  (a) contacting a cell expressing the heteromultimeric acid-sensing ion channel of claim 1 with a candidate compound in the presence of proton ions; and
  (b) determining the ion permeability of the heteromultimeric acid-sensing ion channel in the presence and absence of the candidate compound,
wherein an decrease in the ion permeability in the presence of the candidate compound indicates that the candidate compound is an antagonist of the heteromultimeric acid-sensing ion channel.

* * * * *

SEQUENCE LISTING

<160> NUMBER OF SEQ ID NOS: 28

<210> SEQ ID NO 1
<211> LENGTH: 2748
<212> TYPE: DNA
<213> ORGANISM: HUMAN ASIC2A

<400> SEQUENCE: 1

| | | | | | |
|---|---|---|---|---|---|
| ctcttccaca | tcaccttggt | gtctccctaa | ataaaaccag | ccctccttat | cgcctggaaa | 60 |
| aaatcaagag | ctagagtttg | aatgggtttt | atataaacac | tcacccctgt | cagcgtgcgg | 120 |
| ctgggctctc | aggataaact | cacagcatct | ggcgcgatgc | ttgccttgcg | ttctctcccc | 180 |
| tgaacgtcaa | ggtttaagca | gagcccgagg | actgggagct | cttctctgaa | attcgatcaa | 240 |
| cctgaagcca | gttgcggaac | tgcacggggt | cccgatggac | ctcaaggaaa | gccccagtga | 300 |
| gggcagcctg | caaccttcta | gcatccagat | ctttgccaac | acctccaccc | tccatggcat | 360 |
| ccgccacatc | ttcgtgtatg | gccgctgac | catccggcgt | gtgctgtggg | cagtggcctt | 420 |
| cgtgggctct | ctgggcctgc | tgctggtgga | gagctctgag | agggtgtcct | actacttctc | 480 |
| ctaccagcat | gtcactaagg | tggacgaagt | ggtggctcaa | agcctggtct | cccagctgt | 540 |
| gaccctctgt | aacctsaatg | gcttccggtt | ctccaggctc | accaccaacg | acctgtacca | 600 |
| tgctggggag | ctgctggccc | tgctggatgt | caacctgcag | atcccggacc | ccatctggc | 660 |
| tgacccctcc | gtgctggagg | ccctgcgcgca | gaaggccaac | ttcaagcact | acaaacccaa | 720 |
| gcagttcagc | atgctggagt | tcctgcaccg | tgtgggccat | gacctgaagg | atatgatgct | 780 |
| ctactgcaag | ttcaaagggc | aggagtgcgg | ccaccaagac | ttcaccacag | tgtttacaaa | 840 |
| atatgggaag | tgttacatgt | ttaactcagg | cgaggatggc | aaacctctgc | tcaccacggt | 900 |
| caagggggg | acaggcaacg | ggctggagat | catgctggac | attcagcagg | atgagtacct | 960 |
| gcccatctgg | ggagagacag | aggaaacgac | atttgaagca | ggagtgaaag | ttcagatcca | 1020 |
| cagtcagtct | gagccacctt | tcatccaaga | gctgggcttt | ggggtggctc | cagggttcca | 1080 |
| gacctttgtg | gccacacagg | agcagaggct | cacatacctg | cccccaccgt | ggggtgagtg | 1140 |
| ccgatcctca | gagatgggcc | tcgacttttt | tcctgtttac | agcatcaccg | cctgtaggat | 1200 |
| tgactgtgag | acccgctaca | ttgtggaaaa | ctgcaactgc | cgcatggttc | acatgccagg | 1260 |
| ggatgcccct | ttttgtaccc | ctgagcagca | caaggagtgt | gcagagcctg | ccctaggtct | 1320 |
| gttggcggaa | aaggacagca | attactgtct | ctgcaggaca | ccctgcaacc | taacccgcta | 1380 |
| caacaaagag | ctctccatgg | tgaagatccc | cagcaagaca | tcagccaagt | accttgagaa | 1440 |
| gaaatttaac | aaatcagaaa | aatatatctc | agagaacatc | cttgttctgg | atatattttt | 1500 |
| tgaagctctc | aattatgaga | caattgaaca | gaagaaggcg | tatgaagttg | ctgccttact | 1560 |
| tggtgatatt | ggtggtcaga | tgggattgtt | cattggtgct | agtatcctta | caatactaga | 1620 |
| gctctttgat | tatatttatg | agctgatcaa | agagaagcta | ttagacctgc | ttggcaaaga | 1680 |
| ggaggacgaa | gggagccacg | atgagaatgt | gagtacttgt | gacacaatgc | aaaccactc | 1740 |
| tgaaaccatc | agtcacactg | tgaacgtgcc | cctgcagacg | accctgggga | ccttggagga | 1800 |
| gattgcctgc | tgcacacccct | cgagtcaccc | agcactccct | ccaaacagac | cttgaggccc | 1860 |
| aagacccagg | acaaggaaca | gcaagctcag | gtgggatggc | ccagtgctg | gaaagaagca | 1920 |
| agagcccccct | atgcacacat | tgcagactag | ctgcctagac | ctcgctccgg | ccacgtccaa | 1980 |
| cacgacgcat | ccttgggccc | cgccgtgcgt | ccctcttagg | agagatgagt | cacactctgg | 2040 |

```
aactgtccaa gaacgaacct gccatcacat ctcactgcca gatgtataaa gcacctgcat    2100
gctcagactt cttgtggcgc cacctccacg tctgtcttgt acatgacact cctccacgcg    2160
gtttccagtg tccacactgc tgcccgtgca gtgggaccag attccaggtc caaagtcacc    2220
atgaggccac cctggaatca gaactgcaca atcaagaggg aacccatggg actctctgct    2280
acattcagtt cttgtgtcgt ttgtgaaagt tcttaacctg cccaaaaacc cccttttccc    2340
caagctgccc aygggggcttc ggcgccaaag gtgacccgcg ccaacctccc tcccccccca    2400
gtgcctrtga cggcggcaca gcagccagcg ggtgggggac gcctgtgttc acccatggtg    2460
cccatgtcgt tcttctctcc ctgtgacaca gcttgtacag tctgattctt tttatctggg    2520 gtagggggc ttttatgttt gtccgatgga gatttgtttt gttttgcttc attttatgct    2580 ttttattt agttttgatg ttctgaggtt tgctttggtt tttccatttt ctttggcatt    2640
tatttattcg tgcttcaaat cacagtcata ttaaaagctg gtcttgtgga aaaaaaaaa    2700 aaaaaaaaa aaaaaaaaaa aaaaaaaaa aaaaaaaaaa aaaaaaa                   2748
```

<210> SEQ ID NO 2
<211> LENGTH: 512
<212> TYPE: PRT
<213> ORGANISM: HUMAN ASIC2A

<400> SEQUENCE: 2

```
Met Asp Leu Lys Glu Ser Pro Ser Glu Gly Ser Leu Gln Pro Ser Ser
  1               5                  10                  15

Ile Gln Ile Phe Ala Asn Thr Ser Thr Leu His Gly Ile Arg His Ile
                 20                  25                  30

Phe Val Tyr Gly Pro Leu Thr Ile Arg Arg Val Leu Trp Ala Val Ala
             35                  40                  45

Phe Val Gly Ser Leu Gly Leu Leu Val Glu Ser Ser Glu Arg Val
         50                  55                  60

Ser Tyr Tyr Phe Ser Tyr Gln His Val Thr Lys Val Asp Glu Val Val
 65                  70                  75                  80

Ala Gln Ser Leu Val Phe Pro Ala Val Thr Leu Cys Asn Leu Asn Gly
                 85                  90                  95

Phe Arg Phe Ser Arg Leu Thr Thr Asn Asp Leu Tyr His Ala Gly Glu
            100                 105                 110

Leu Leu Ala Leu Leu Asp Val Asn Leu Gln Ile Pro Asp Pro His Leu
        115                 120                 125

Ala Asp Pro Ser Val Leu Glu Ala Leu Arg Gln Lys Ala Asn Phe Lys
    130                 135                 140

His Tyr Lys Pro Lys Gln Phe Ser Met Leu Glu Phe Leu His Arg Val
145                 150                 155                 160

Gly His Asp Leu Lys Asp Met Met Leu Tyr Cys Lys Phe Lys Gly Gln
                165                 170                 175

Glu Cys Gly His Gln Asp Phe Thr Thr Val Phe Thr Lys Tyr Gly Lys
            180                 185                 190

Cys Tyr Met Phe Asn Ser Gly Glu Asp Gly Lys Pro Leu Leu Thr Thr
        195                 200                 205

Val Lys Gly Gly Thr Gly Asn Gly Leu Glu Ile Met Leu Asp Ile Gln
    210                 215                 220

Gln Asp Glu Tyr Leu Pro Ile Trp Gly Glu Thr Glu Glu Thr Thr Phe
225                 230                 235                 240

Glu Ala Gly Val Lys Val Gln Ile His Ser Gln Ser Glu Pro Pro Phe
```

-continued

```
                245                 250                 255
Ile Gln Glu Leu Gly Phe Gly Val Ala Pro Gly Phe Gln Thr Phe Val
                260                 265                 270

Ala Thr Gln Glu Gln Arg Leu Thr Tyr Leu Pro Pro Trp Gly Glu
            275                 280                 285

Cys Arg Ser Ser Glu Met Gly Leu Asp Phe Phe Pro Val Tyr Ser Ile
        290                 295                 300

Thr Ala Cys Arg Ile Asp Cys Glu Thr Arg Tyr Ile Val Glu Asn Cys
305                 310                 315                 320

Asn Cys Arg Met Val His Met Pro Gly Asp Ala Pro Phe Cys Thr Pro
                325                 330                 335

Glu Gln His Lys Glu Cys Ala Glu Pro Ala Leu Gly Leu Leu Ala Glu
            340                 345                 350

Lys Asp Ser Asn Tyr Cys Leu Cys Arg Thr Pro Cys Asn Leu Thr Arg
        355                 360                 365

Tyr Asn Lys Glu Leu Ser Met Val Lys Ile Pro Ser Lys Thr Ser Ala
    370                 375                 380

Lys Tyr Leu Glu Lys Lys Phe Asn Lys Ser Glu Lys Tyr Ile Ser Glu
385                 390                 395                 400

Asn Ile Leu Val Leu Asp Ile Phe Phe Glu Ala Leu Asn Tyr Glu Thr
                405                 410                 415

Ile Glu Gln Lys Lys Ala Tyr Glu Val Ala Ala Leu Leu Gly Asp Ile
            420                 425                 430

Gly Gly Gln Met Gly Leu Phe Ile Gly Ala Ser Ile Leu Thr Ile Leu
        435                 440                 445

Glu Leu Phe Asp Tyr Ile Tyr Glu Leu Ile Lys Glu Lys Leu Leu Asp
    450                 455                 460

Leu Leu Gly Lys Glu Glu Asp Glu Gly Ser His Asp Glu Asn Val Ser
465                 470                 475                 480

Thr Cys Asp Thr Met Pro Asn His Ser Glu Thr Ile Ser His Thr Val
                485                 490                 495

Asn Val Pro Leu Gln Thr Thr Leu Gly Thr Leu Glu Glu Ile Ala Cys
            500                 505                 510

<210> SEQ ID NO 3
<211> LENGTH: 1732
<212> TYPE: DNA
<213> ORGANISM: HUMAN ASIC3

<400> SEQUENCE: 3
tcgcacgacg cggttctggc catgaagccc acctcaggcc cagaggaggc ccggcggcag      60
ccctcggaca tccgcgtgtt cgccagcaac tgctcgatgc acgggctggg ccacgtcttc     120
gggccaggca gcctgagcct gcgccggggg atgtgggcag cggccgtggt cctgtcagtg     180
gccaccttcc tctaccaggt ggctgagagg gtgcgctact acaggagtt ccaccaccag      240 actgccctgg atgagcgaga aagccaccgg ctcgtcttcc cggctgtcac cctgtgcaac     300
atcaacccac tgcgccgctc gcgcctaacg cccaacgacc tgcactgggc tgggtctgcg     360
ctgctgggcc tggatcccgc agagcacgcc gccttcctgc gcgccctggg ccggccccct     420
gcaccgcccg gcttcatgcc cagtcccacc tttgacatgg cgcaactcta tgcccgtgct     480
gggcactccc tggatgacat gctgctggac tgtcgcttcc gtggccaacc ttgtgggcct     540
gagaacttca ccacgatctt cacccggatg gaaagtgct acacatttaa ctctggcgct    600 gatgggggcag agctgctcac cactactagg ggtggcatgg caatgggct ggacatcatg    660
```

```
ctggacgtgc agcaggagga atatctacct gtgtggaggg acaatgagga gaccccgttt    720
gaggtgggga tccgagtgca gatccacagc caggaggagc cgcccatcat cgatcagctg    780
ggcttggggg tgtccccggg ctaccagacc tttgtttctt gccagcagca gcagctgagc    840
ttcctgccac cgccctgggg cgattgcagt tcagcatctc tgaaccccaa ctatgagcca    900
gagccctctg atccctagg ctcccccagc cccagcccca gccctcccta taccctttatg    960
gggtgtcgcc tggcctgcga aacccgctac gtggctcgga agtgcggctg ccgaatggtg   1020
tacatgccag cgacgtgcc agtgtgcagc ccccagcagt acaagaactg tgcccacccg   1080
gccatagatg ccatccttcg caaggactcg tgcgcctgcc caacccgtg cgccagcacg   1140
cgctacgcca aggagctctc catggtgcgg atcccgagcc gcgccgccgc gcgcttcctg   1200
gcccggaagc tcaaccgcag cgaggcctac atcgcggaga acgtgctggc cctggacatc   1260
ttctttgagg ccctcaacta tgagaccgtg gagcagaaga aggcctatga gatgtcagag   1320
ctgcttggtg acattggggg ccagatgggc cttttcatcg gggccagcct gctcaccatc   1380
ctcgagatcc tagactacct ctgtgaggtg ttccgagaca aggtcctggg atatttctgg   1440
aaccgacagc actcccaaag gcactccagc accaatctgc ttcaggaagg gctgggcagc   1500
catcgaaccc aagttcccca cctcagcctg ggcccagac ctcccacccc tccctgtgcc   1560
gtcaccaaga ctctctccgc ctcccaccgc acctgctacc ttgtcacaca gctctagacc   1620
tgctgtctgt gtcctcggag ccccgccctg acatcctgga catgcctagc ctgcacgtag   1680
cttttccgtc ttcaccccaa ataaagtcct aatgcatcaa aaaaaaaaa aa            1732
```

<210> SEQ ID NO 4
<211> LENGTH: 531
<212> TYPE: PRT
<213> ORGANISM: HUMAN ASIC3

<400> SEQUENCE: 4

```
Met Lys Pro Thr Ser Gly Pro Glu Glu Ala Arg Arg Gln Pro Ser Asp
  1               5                  10                  15

Ile Arg Val Phe Ala Ser Asn Cys Ser Met His Gly Leu Gly His Val
             20                  25                  30

Phe Gly Pro Gly Ser Leu Ser Leu Arg Arg Gly Met Trp Ala Ala Ala
         35                  40                  45

Val Val Leu Ser Val Ala Thr Phe Leu Tyr Gln Val Ala Glu Arg Val
     50                  55                  60

Arg Tyr Tyr Arg Glu Phe His His Gln Thr Ala Leu Asp Glu Arg Glu
 65                  70                  75                  80

Ser His Arg Leu Val Phe Pro Ala Val Thr Leu Cys Asn Ile Asn Pro
                 85                  90                  95

Leu Arg Arg Ser Arg Leu Thr Pro Asn Asp Leu His Trp Ala Gly Ser
            100                 105                 110

Ala Leu Leu Gly Leu Asp Pro Ala Glu His Ala Ala Phe Leu Arg Ala
        115                 120                 125

Leu Gly Arg Pro Pro Ala Pro Pro Gly Phe Met Pro Ser Pro Thr Phe
    130                 135                 140

Asp Met Ala Gln Leu Tyr Ala Arg Ala Gly His Ser Leu Asp Asp Met
145                 150                 155                 160

Leu Leu Asp Cys Arg Phe Arg Gly Gln Pro Cys Gly Pro Glu Asn Phe
                165                 170                 175

Thr Thr Ile Phe Thr Arg Met Gly Lys Cys Tyr Thr Phe Asn Ser Gly
```

-continued

```
            180             185             190
Ala Asp Gly Ala Glu Leu Leu Thr Thr Thr Arg Gly Gly Met Gly Asn
            195                 200                 205
Gly Leu Asp Ile Met Leu Asp Val Gln Gln Glu Glu Tyr Leu Pro Val
        210                 215                 220
Trp Arg Asp Asn Glu Glu Thr Pro Phe Glu Val Gly Ile Arg Val Gln
225                 230                 235                 240
Ile His Ser Gln Glu Glu Pro Pro Ile Ile Asp Gln Leu Gly Leu Gly
                245                 250                 255
Val Ser Pro Gly Tyr Gln Thr Phe Val Ser Cys Gln Gln Gln Leu
        260                 265                 270
Ser Phe Leu Pro Pro Pro Trp Gly Asp Cys Ser Ser Ala Ser Leu Asn
        275                 280                 285
Pro Asn Tyr Glu Pro Glu Pro Ser Asp Pro Leu Gly Ser Pro Ser Pro
        290                 295                 300
Ser Pro Ser Pro Pro Tyr Thr Leu Met Gly Cys Arg Leu Ala Cys Glu
305                 310                 315                 320
Thr Arg Tyr Val Ala Arg Lys Cys Gly Cys Arg Met Val Tyr Met Pro
                325                 330                 335
Gly Asp Val Pro Val Cys Ser Pro Gln Gln Tyr Lys Asn Cys Ala His
            340                 345                 350
Pro Ala Ile Asp Ala Ile Leu Arg Lys Asp Ser Cys Ala Cys Pro Asn
        355                 360                 365
Pro Cys Ala Ser Thr Arg Tyr Ala Lys Glu Leu Ser Met Val Arg Ile
        370                 375                 380
Pro Ser Arg Ala Ala Arg Phe Leu Ala Arg Lys Leu Asn Arg Ser
385                 390                 395                 400
Glu Ala Tyr Ile Ala Glu Asn Val Leu Ala Leu Asp Ile Phe Phe Glu
                405                 410                 415
Ala Leu Asn Tyr Glu Thr Val Glu Gln Lys Lys Ala Tyr Glu Met Ser
            420                 425                 430
Glu Leu Leu Gly Asp Ile Gly Gly Gln Met Gly Leu Phe Ile Gly Ala
        435                 440                 445
Ser Leu Leu Thr Ile Leu Glu Ile Leu Asp Tyr Leu Cys Glu Val Phe
        450                 455                 460
Arg Asp Lys Val Leu Gly Tyr Phe Trp Asn Arg Gln His Ser Gln Arg
465                 470                 475                 480
His Ser Ser Thr Asn Leu Leu Gln Glu Gly Leu Gly Ser His Arg Thr
                485                 490                 495
Gln Val Pro His Leu Ser Leu Gly Pro Arg Pro Pro Thr Pro Pro Cys
            500                 505                 510
Ala Val Thr Lys Thr Leu Ser Ala Ser His Arg Thr Cys Tyr Leu Val
            515                 520                 525
Thr Gln Leu
    530

<210> SEQ ID NO 5
<211> LENGTH: 2565
<212> TYPE: DNA
<213> ORGANISM: RAT ASIC2A

<400> SEQUENCE: 5
caggctctca ggataactcc cagtgtctgg cctgatgctt gcctggcgat ctctgccttg      60
aatgccaagg tttaagcaga attcagagga ctgagaactc ttccctgaga tttgatcaac     120
```

```
ctgaagccag ttgcagaact gcacagggtc ccgatggacc tcaaggagag ccccagtgag      180
ggcagcctgc aaccttccag tatccagatc ttcgccaata cctccactct ccatggcatc      240
cgccacatct tcgtgtatgg gccgctgacc atccggcgtg tgctttgggc agtggccttc      300
gtcggatccc tgggcctgct gctggtggag agctcggaga gggtgtccta ctatttctct      360
tatcagcatg ttaccaaggt ggatgaagtg gtgcccaga gcctggtctt cccagctgtg       420
accctctgca acctcaatgg cttccggttc tccaggctta ccaccaacga cttgtaccac      480
gctggggagt gctggccct gctggatgtc aacctacaga ttcccgaccc gcatctggca       540
gaccccacgg tgctggaggc cctccgacag aaggccaact tcaaacacta caaaccgaag      600
cagttcagca tgctggagtt cctgcaccgg gtaggccatg acctgaagga tatgatgctc      660
tactgcaagt tcaaggggca ggagtgtggg catcaagact tcaccacagt gtttacaaaa      720
tacgggaagt gttacatgtt taactcaggc gaggatggca agccgctgct caccacggtc      780
aaggggggga cgggcaacgg gctggagatc atgctggaca ttcagcaaga tgagtacctg      840
cccatctggg gagagacaga ggaaacaacg tttgaagcag gagtgaaggt tcagatccac      900
agtcagtctg agccgccttt catccaagag ctgggctttg gggtggctcc ggggttccag      960
accttcgtgg ccacacaaga gcagaggctc acatatctgc ccccaccatg ggggagtgc      1020 cggtcctcag agatgggact cgacttcttt cctgtttaca gcatcacagc ctgtcggatt      1080
gactgtgaga cccgctacat cgtggagaac tgtaactgcc gcatggtcca catgccaggg      1140 gacgccctt tctgcacccc tgagcagcac aaggagtgtg cagagcctgc cctcggtcta      1200
ctggcagaaa aggacagcaa ttactgtctc tgcaggacac cctgcaacct gacacgctac      1260
aacaaagagc tctccatggt gaagatcccc agcaagacgt cagccaagta cttagagaag      1320
aaatttaaca aatcggaaaa atatatctca gagaacattc ttgttctgga catatttttt      1380
gaggcgctca attacgaaac aattgaacag aagaaggcgt atgaagttgc tgccttactt      1440
ggtgacatcg gtggtcagat gggactgttc attggtgcta gtctcctcac aatactagag      1500
ctctttgatt atatttatga gctgatcaaa gagaagctat tagacctgct tggcaaagaa      1560
gaagaggaag ggagccacga tgagaacatg agcacctgtg acacaatgcc aaaccactct      1620
gaaaccatca gccacactgt gaacgtgccc ctgcagacag cttttgggcac cctggaggag     1680 attgcctgct gacacctctc aggcaacgca gcacctccaa acagaccttta aaggcccaag    1740 acctaggaca ggagacagca agcgcaggtg ggatcgcccc tgacgactga agaagcaga      1800 gccccccata tgcacacatt gcgaacttct gccaaacctc acctggccac atctgacatg     1860
aaccgtcccg ggccctgcgt catgtccctc gcaggaccga tgagtcgcac tccggaactg     1920
tccaagaact aacctgccat cacatctcac tgccagatgt acaaagcacc tgcatgctca    1980
gacttcttac agcgccacct ccacttccga cttgtacgtg atattttctc cgtgcggttt     2040
ccagggccca ctccgctgcc caggcaatgg gaccaggttc cagccccaaa gtcaccctga    2100
gcccagctcc ggaatcgaaa ctgcacagtc aagaaggaaa ccacagaact ctctacgttt    2160
gatccttgtg ttgtttgtga ccgttcttag ccttgtcctc caaactggcc caaggggcta    2220
ctgcactaaa ggtgaccagt accaacctcc ttcttttccc agcacccgtg aaggaggtac    2280
agtggcccgg gtgaccccag tatttgtcca tggagccaca ttgttctctc cctgtgacac    2340
agctgtagag tctgatttg ttttgttttg ttttgtttag ggcggggact ttttttgttt     2400
gtctatggaa gatttgtttt gttccgcttt gtcttacggt cttcggtttt gatgttctaa    2460
```

```
ggttcgaatt gggttttcca ttttttttt tgagtttatt tattcgtgct tcgaaccaca    2520
gtcatattaa aagctggtct tgtggaaaaa aaaaaaaaaa aaaaa                   2565
```

<210> SEQ ID NO 6
<211> LENGTH: 512
<212> TYPE: PRT
<213> ORGANISM: RAT ASIC2A

<400> SEQUENCE: 6

```
Met Asp Leu Lys Glu Ser Pro Ser Glu Gly Ser Leu Gln Pro Ser Ser
 1               5                   10                  15

Ile Gln Ile Phe Ala Asn Thr Ser Thr Leu His Gly Ile Arg His Ile
            20                  25                  30

Phe Val Tyr Gly Pro Leu Thr Ile Arg Arg Val Leu Trp Ala Val Ala
        35                  40                  45

Phe Val Gly Ser Leu Gly Leu Leu Val Glu Ser Ser Glu Arg Val
    50                  55                  60

Ser Tyr Tyr Phe Ser Tyr Gln His Val Thr Lys Val Asp Glu Val Val
65                  70                  75                  80

Ala Gln Ser Leu Val Phe Pro Ala Val Thr Leu Cys Asn Leu Asn Gly
                85                  90                  95

Phe Arg Phe Ser Arg Leu Thr Thr Asn Asp Leu Tyr His Ala Gly Glu
            100                 105                 110

Leu Leu Ala Leu Leu Asp Val Asn Leu Gln Ile Pro Asp Pro His Leu
        115                 120                 125

Ala Asp Pro Thr Val Leu Glu Ala Leu Arg Gln Lys Ala Asn Phe Lys
    130                 135                 140

His Tyr Lys Pro Lys Gln Phe Ser Met Leu Glu Phe Leu His Arg Val
145                 150                 155                 160

Gly His Asp Leu Lys Asp Met Met Leu Tyr Cys Lys Phe Lys Gly Gln
                165                 170                 175

Glu Cys Gly His Gln Asp Phe Thr Thr Val Phe Thr Lys Tyr Gly Lys
            180                 185                 190

Cys Tyr Met Phe Asn Ser Gly Glu Asp Gly Lys Pro Leu Leu Thr Thr
        195                 200                 205

Val Lys Gly Gly Thr Gly Asn Gly Leu Glu Ile Met Leu Asp Ile Gln
    210                 215                 220

Gln Asp Glu Tyr Leu Pro Ile Trp Gly Glu Thr Glu Thr Thr Phe
225                 230                 235                 240

Glu Ala Gly Val Lys Val Gln Ile His Ser Gln Ser Glu Pro Pro Phe
                245                 250                 255

Ile Gln Glu Leu Gly Phe Gly Val Ala Pro Gly Phe Gln Thr Phe Val
            260                 265                 270

Ala Thr Gln Glu Gln Arg Leu Thr Tyr Leu Pro Pro Pro Trp Gly Glu
        275                 280                 285

Cys Arg Ser Ser Glu Met Gly Leu Asp Phe Phe Pro Val Tyr Ser Ile
    290                 295                 300

Thr Ala Cys Arg Ile Asp Cys Glu Thr Arg Tyr Ile Val Glu Asn Cys
305                 310                 315                 320

Asn Cys Arg Met Val His Met Pro Gly Asp Ala Pro Phe Cys Thr Pro
                325                 330                 335

Glu Gln His Lys Glu Cys Ala Glu Pro Ala Leu Gly Leu Leu Ala Glu
            340                 345                 350

Lys Asp Ser Asn Tyr Cys Leu Cys Arg Thr Pro Cys Asn Leu Thr Arg
```

|  | 355 |  |  | 360 |  |  | 365 |  |  |  |
|---|---|---|---|---|---|---|---|---|---|---|
| Tyr | Asn | Lys | Glu | Leu | Ser | Met | Val | Lys | Ile | Pro | Ser | Lys | Thr | Ser | Ala |
|  | 370 |  |  |  | 375 |  |  |  | 380 |  |

Tyr Asn Lys Glu Leu Ser Met Val Lys Ile Pro Ser Lys Thr Ser Ala
     370               375               380

Lys Tyr Leu Glu Lys Lys Phe Asn Lys Ser Glu Lys Tyr Ile Ser Glu
385               390               395               400

Asn Ile Leu Val Leu Asp Ile Phe Phe Glu Ala Leu Asn Tyr Glu Thr
              405               410               415

Ile Glu Gln Lys Lys Ala Tyr Glu Val Ala Ala Leu Leu Gly Asp Ile
           420               425               430

Gly Gly Gln Met Gly Leu Phe Ile Gly Ala Ser Leu Leu Thr Ile Leu
              435               440               445

Glu Leu Phe Asp Tyr Ile Tyr Glu Leu Ile Lys Glu Lys Leu Leu Asp
450               455               460

Leu Leu Gly Lys Glu Glu Glu Gly Ser His Asp Glu Asn Met Ser
465               470               475               480

Thr Cys Asp Thr Met Pro Asn His Ser Glu Thr Ile Ser His Thr Val
              485               490               495

Asn Val Pro Leu Gln Thr Ala Leu Gly Thr Leu Glu Glu Ile Ala Cys
     500               505               510

<210> SEQ ID NO 7
<211> LENGTH: 1602
<212> TYPE: DNA
<213> ORGANISM: RAT ASIC3

<400> SEQUENCE: 7

```
atgaaacctc gctccggact ggaggaggcc cagcggcgac aggcctcaga catccgggtg      60
tttgccagca gctgcacaat gcatggtctg ggccacatct tggccctgg aggcctgacc     120
ctgcgccgag ggctgtgggc cacagctgtg ctcctgtcgc tggcggcctt cctctaccag     180
gtggctgagc gggttcgcta ctatggggag ttccaccata gaccaccct ggatgagcgt      240
gagagccacc agctcacctt cccagctgtg actctgtgta atatcaaccc actgcgccgc     300
tcacgcctca cacccaatga cttgcactgg gctggaacag cgctgctggg cctgaccct      360
gctgaacatg ctgcctacct tcgtgcactg ggccagcccc ccgcaccacc tggcttcatg     420
cccagtccga ccttt gacat ggcacaactc tacgccagag ccggccactc ccttgaggac     480
atgttgttgg attgccgata ccgtggccag ccctgtgggc ctgagaactt cacagtgatc     540
tttactcgaa tggggcaatg ctacaccttc aactctggtg cccacggtgc agagctgctc     600
accactccaa agggtggtgc tggcaacgga ctggagatta tgctagatgt acagcaagag     660
gagtatctgc ccatctggaa ggacatggaa gagaccccgt ttgaggtggg gatccgagtg     720
cagattcaca gccaggatga gcccctgcc attgaccagc tgggcttcgg ggcagcccca     780
ggccatcaga cttttgtgtc ctgtcagcag cagcaactga gtttcctgcc accaccctgg     840
ggtgactgca ataccgcatc tttggatccc gacgactttg atccagagcc ctctgatccc     900
ttgggttccc ccagacccag acccagccct cctatagtt taataggttg tcgcctggcc     960
tgtgagtctc gctatgtggc tcggaagtgt ggctgtcgaa tgatgcatat gcctggaaac    1020
tccccagtgt gcagccccca gcagtacaag gactgcgcca gcccagctct ggacgctatg    1080
ctgcgaaagg acacgtgtgt ctgccccaac ccgtgcgcta ctacacgcta tgccaaggag    1140
ctctccatgg tgcggattcc agccgcgcg tcagctcgct acctggcccg gaaatacaac    1200
cgcagcgagt cctacattac ggagaatgta ctggttctgg atatcttctt tgaggccctc    1260
```

-continued

```
aactatgaag cggtggaaca aaaggcggcc tatgaagtgt cggagctgct gggagacatt    1320
gggggacaga tgggactgtt tattggagca agcctgctta ccatccttga gatcctcgac    1380
tatctctgtg aggttttcca agacagagtc ctggggtatt tctggaacag aaggagcgct    1440
caaaagcgct ctggcaacac tctgctccag gaagagttga atggccatcg aacacatgtt    1500
ccccacctca gcctagggcc caggcctcct accactccct gtgctgtcac caagacactc    1560
tctgcctccc accgtacctg ttacctcgtc acaaggctct ag                       1602
```

<210> SEQ ID NO 8
<211> LENGTH: 533
<212> TYPE: PRT
<213> ORGANISM: RAT ASIC2A

<400> SEQUENCE: 8

```
Met Lys Pro Arg Ser Gly Leu Glu Glu Ala Gln Arg Arg Gln Ala Ser
 1               5                  10                  15

Asp Ile Arg Val Phe Ala Ser Ser Cys Thr Met His Gly Leu Gly His
            20                  25                  30

Ile Phe Gly Pro Gly Gly Leu Thr Leu Arg Arg Gly Leu Trp Ala Thr
        35                  40                  45

Ala Val Leu Leu Ser Leu Ala Ala Phe Leu Tyr Gln Val Ala Glu Arg
    50                  55                  60

Val Arg Tyr Tyr Gly Glu Phe His His Lys Thr Thr Leu Asp Glu Arg
65                  70                  75                  80

Glu Ser His Gln Leu Thr Phe Pro Ala Val Thr Leu Cys Asn Ile Asn
                85                  90                  95

Pro Leu Arg Arg Ser Arg Leu Thr Pro Asn Asp Leu His Trp Ala Gly
            100                 105                 110

Thr Ala Leu Leu Gly Leu Asp Pro Ala Glu His Ala Ala Tyr Leu Arg
        115                 120                 125

Ala Leu Gly Gln Pro Pro Ala Pro Pro Gly Phe Met Pro Ser Pro Thr
    130                 135                 140

Phe Asp Met Ala Gln Leu Tyr Ala Arg Ala Gly His Ser Leu Glu Asp
145                 150                 155                 160

Met Leu Leu Asp Cys Arg Tyr Arg Gly Gln Pro Cys Gly Pro Glu Asn
                165                 170                 175

Phe Thr Val Ile Phe Thr Arg Met Gly Gln Cys Tyr Thr Phe Asn Ser
            180                 185                 190

Gly Ala His Gly Ala Glu Leu Leu Thr Thr Pro Lys Gly Gly Ala Gly
        195                 200                 205

Asn Gly Leu Glu Ile Met Leu Asp Val Gln Gln Glu Glu Tyr Leu Pro
    210                 215                 220

Ile Trp Lys Asp Met Glu Glu Thr Pro Phe Glu Val Gly Ile Arg Val
225                 230                 235                 240

Gln Ile His Ser Gln Asp Glu Pro Pro Ala Ile Asp Gln Leu Gly Phe
                245                 250                 255

Gly Ala Ala Pro Gly His Gln Thr Phe Val Ser Cys Gln Gln Gln Gln
            260                 265                 270

Leu Ser Phe Leu Pro Pro Pro Trp Gly Asp Cys Asn Thr Ala Ser Leu
        275                 280                 285

Asp Pro Asp Asp Phe Asp Pro Glu Pro Ser Asp Pro Leu Gly Ser Pro
    290                 295                 300

Arg Pro Arg Pro Ser Pro Pro Tyr Ser Leu Ile Gly Cys Arg Leu Ala
305                 310                 315                 320
```

```
Cys Glu Ser Arg Tyr Val Ala Arg Lys Cys Gly Cys Arg Met Met His
                325                 330                 335
Met Pro Gly Asn Ser Pro Val Cys Ser Pro Gln Gln Tyr Lys Asp Cys
                340                 345                 350
Ala Ser Pro Ala Leu Asp Ala Met Leu Arg Lys Asp Thr Cys Val Cys
                355                 360                 365
Pro Asn Pro Cys Ala Thr Thr Arg Tyr Ala Lys Glu Leu Ser Met Val
            370                 375                 380
Arg Ile Pro Ser Arg Ala Ser Ala Arg Tyr Leu Ala Arg Lys Tyr Asn
385                 390                 395                 400
Arg Ser Glu Ser Tyr Ile Thr Glu Asn Val Leu Val Leu Asp Ile Phe
                405                 410                 415
Phe Glu Ala Leu Asn Tyr Glu Ala Val Glu Gln Lys Ala Ala Tyr Glu
                420                 425                 430
Val Ser Glu Leu Leu Gly Asp Ile Gly Gly Gln Met Gly Leu Phe Ile
                435                 440                 445
Gly Ala Ser Leu Leu Thr Ile Leu Glu Ile Leu Asp Tyr Leu Cys Glu
            450                 455                 460
Val Phe Gln Asp Arg Val Leu Gly Tyr Phe Trp Asn Arg Arg Ser Ala
465                 470                 475                 480
Gln Lys Arg Ser Gly Asn Thr Leu Leu Gln Glu Glu Leu Asn Gly His
                485                 490                 495
Arg Thr His Val Pro His Leu Ser Leu Gly Pro Arg Pro Thr Thr Thr
                500                 505                 510
Pro Cys Ala Val Thr Lys Thr Leu Ser Ala Ser His Arg Thr Cys Tyr
            515                 520                 525
Leu Val Thr Arg Leu
        530

<210> SEQ ID NO 9
<211> LENGTH: 20
<212> TYPE: DNA
<213> ORGANISM: HUMAN ASIC3

<400> SEQUENCE: 9
aggtgttccg agacaaggtc                                            20

<210> SEQ ID NO 10
<211> LENGTH: 31
<212> TYPE: DNA
<213> ORGANISM: HUMAN ASIC3

<400> SEQUENCE: 10
gcgaattccg agagctgtgt gacaaggtag c                               31

<210> SEQ ID NO 11
<211> LENGTH: 20
<212> TYPE: DNA
<213> ORGANISM: HUMAN ASIC2A

<400> SEQUENCE: 11
tctttgccaa cacctccacc                                            20

<210> SEQ ID NO 12
<211> LENGTH: 20
<212> TYPE: DNA
<213> ORGANISM: HUMAN ASIC2A
```

```
<400> SEQUENCE: 12
ctcctgccct ttgaacttgc                                                    20

<210> SEQ ID NO 13
<211> LENGTH: 18
<212> TYPE: DNA
<213> ORGANISM: HUMAN ASIC3

<400> SEQUENCE: 13
agtggccacc ttcctcta                                                      18

<210> SEQ ID NO 14
<211> LENGTH: 20
<212> TYPE: DNA
<213> ORGANISM: HUMAN ASIC3

<400> SEQUENCE: 14
cagtccagca gcatgtcatc                                                    20

<210> SEQ ID NO 15
<211> LENGTH: 29
<212> TYPE: DNA
<213> ORGANISM: HUMAN ASIC3

<400> SEQUENCE: 15
tccaagctta tgggatattt ctggaaccg                                          29

<210> SEQ ID NO 16
<211> LENGTH: 28
<212> TYPE: DNA
<213> ORGANISM: HUMAN ASIC3

<400> SEQUENCE: 16
cgggatccaa agctacgtgc aggctagg                                           28

<210> SEQ ID NO 17
<211> LENGTH: 31
<212> TYPE: DNA
<213> ORGANISM: HUMAN ASIC2A

<400> SEQUENCE: 17
tccaagctta tgcttggcaa agaggaggac g                                       31

<210> SEQ ID NO 18
<211> LENGTH: 28
<212> TYPE: DNA
<213> ORGANISM: HUMAN ASIC2A

<400> SEQUENCE: 18
cgggatccga gcttgctgtt ccttgtcc                                           28

<210> SEQ ID NO 19
<211> LENGTH: 192
<212> TYPE: DNA
<213> ORGANISM: HUMAN ASIC3

<400> SEQUENCE: 19
atgggatatt tctggaaccg acagcactcc caaaggcact ccagcaccaa tctgcttcag        60
gaagggctgg gcagccatcg aacccaagtt ccccacctca gcctgggccc cagacctccc       120 accctccct gtgccgtcac caagactctc tccgcctccc accgcacctg ctaccttgtc        180
acacagctct ag                                                           192
```

<210> SEQ ID NO 20
<211> LENGTH: 64
<212> TYPE: PRT
<213> ORGANISM: HUMAN ASIC3

<400> SEQUENCE: 20

Met Leu Gly Tyr Phe Trp Asn Arg Gln His Ser Gln Arg His Ser Ser
1               5                   10                  15

Thr Asn Leu Leu Gln Glu Gly Leu Gly Ser His Arg Thr Gln Val Pro
                20                  25                  30

His Leu Ser Leu Gly Pro Arg Pro Thr Pro Cys Ala Val Thr
        35                  40                  45

Lys Thr Leu Ser Ala Ser His Arg Thr Cys Tyr Leu Val Thr Gln Leu
        50                  55                  60

<210> SEQ ID NO 21
<211> LENGTH: 147
<212> TYPE: DNA
<213> ORGANISM: HUMAN ASIC2A

<400> SEQUENCE: 21
atgcttggca aagaggagga cgaagggagc cacgatgaga atgtgagtac ttgtgacaca    60
atgccaaacc actctgaaac catcagtcac actgtgaacg tgcccctgca gacgacccotg  120 gggaccttgg aggagattgc ctgctga                                       147

<210> SEQ ID NO 22
<211> LENGTH: 48
<212> TYPE: PRT
<213> ORGANISM: HUMAN ASIC2A

<400> SEQUENCE: 22

Met Leu Gly Lys Glu Glu Asp Glu Gly Ser His Asp Glu Asn Val Ser
1               5                   10                  15

Thr Cys Asp Thr Met Pro Asn His Ser Glu Thr Ile Ser His Thr Val
                20                  25                  30

Asn Val Pro Leu Gln Thr Thr Leu Gly Thr Leu Glu Glu Ile Ala Cys
        35                  40                  45

<210> SEQ ID NO 23
<211> LENGTH: 25
<212> TYPE: DNA
<213> ORGANISM: HUMAN ASIC3

<400> SEQUENCE: 23
ggatgtgggc ataggccgtg gtcct                                          25

<210> SEQ ID NO 24
<211> LENGTH: 24
<212> TYPE: DNA
<213> ORGANISM: HUMAN ASIC2A

<400> SEQUENCE: 24
cgtgtgctgt gagcagtggc cttc                                           24

<210> SEQ ID NO 25
<211> LENGTH: 152
<212> TYPE: DNA
<213> ORGANISM: HUMAN ASIC3

<400> SEQUENCE: 25

-continued

```
atgaagccca cctcaggccc agaggaggcc cggcggcagc cctcggacat ccgcgtgttc    60
gccagcaact gctcgatgca cgggctgggc cacgtcttcg ggccaggcag cctgagcctg   120
cgccggggga tgtgggcata ggccgtggtc ct                                 152
```

<210> SEQ ID NO 26
<211> LENGTH: 46
<212> TYPE: PRT
<213> ORGANISM: HUMAN ASIC3

<400> SEQUENCE: 26

Met Lys Pro Thr Ser Gly Pro Glu Glu Ala Arg Arg Gln Pro Ser Asp
1               5                   10                  15

Ile Arg Val Phe Ala Ser Asn Cys Ser Met His Gly Leu Gly His Val
            20                  25                  30

Phe Gly Pro Gly Ser Leu Ser Leu Arg Arg Gly Met Trp Ala
        35                  40                  45

<210> SEQ ID NO 27
<211> LENGTH: 147
<212> TYPE: DNA
<213> ORGANISM: HUMAN ASIC2A

<400> SEQUENCE: 27

```
atggacctca aggagagccc cagtgagggc agcctgcaac cttccagtat ccagatcttc    60
gccaatacct ccactctcca tggcatccgc acatcttcg tgtatgggcc gctgaccatc   120
cggcgtgtgc tttgagcagt ggccttc                                       147
```

<210> SEQ ID NO 28
<211> LENGTH: 44
<212> TYPE: PRT
<213> ORGANISM: HUMAN ASIC2A

<400> SEQUENCE: 28

Met Asp Leu Lys Glu Ser Pro Ser Glu Gly Ser Leu Gln Pro Ser Ser
1               5                   10                  15

Ile Gln Ile Phe Ala Asn Thr Ser Thr Leu His Gly Ile Arg His Ile
            20                  25                  30

Phe Val Tyr Gly Pro Leu Thr Ile Arg Arg Val Leu
        35                  40